United States Patent
Pachuk et al.

(10) Patent No.: US 7,897,382 B2
(45) Date of Patent: *Mar. 1, 2011

(54) TRANSFECTION KINETICS AND STRUCTURAL PROMOTERS

(75) Inventors: Catherine J. Pachuk, Lansdale, PA (US); Chandrasekhar Satishchandran, Lansdale, PA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 228 days.

This patent is subject to a terminal disclaimer.

(21) Appl. No.: 12/034,541

(22) Filed: Feb. 20, 2008

(65) Prior Publication Data

US 2009/0081654 A1 Mar. 26, 2009

Related U.S. Application Data

(63) Continuation of application No. 10/829,747, filed on Apr. 22, 2004, now Pat. No. 7,527,945, which is a continuation-in-part of application No. PCT/US02/33669, filed on Oct. 22, 2002.

(60) Provisional application No. 60/464,434, filed on Apr. 22, 2003, provisional application No. 60/342,788, filed on Oct. 22, 2001.

(51) Int. Cl.
*C12N 15/00* (2006.01)
(52) U.S. Cl. .................. 435/320.1; 435/91.1; 536/24.1
(58) Field of Classification Search .............. None
See application file for complete search history.

(56) References Cited

U.S. PATENT DOCUMENTS 7,527,945 B2 * 5/2009 Pachuk et al. .............. 435/69.1
2002/0155989 A1 10/2002 Efimov et al.

FOREIGN PATENT DOCUMENTS

| WO | WO 94/17086 | 8/1994 |
| WO | WO 95/22623 | 8/1995 |
| WO | WO 99/09045 | 2/1999 |
| WO | WO 01/04313 | 1/2001 |
| WO | WO 02/50264 | 6/2002 |
| WO | WO 03/035910 | 5/2003 |

OTHER PUBLICATIONS

Baner et al., "More keys to padlock probes: mechanisms for high-throughput nucleic acid analysis," Current Opinion in Biotechnology, pp. 11-15, (Feb. 2001), XP002244472.
Bentin et al., "Enhanced peptide nucleic acid binding to supercoiled DNA: possible implications for DNA breathing dynamics", Biochemistry, 35(27), pp. 8863-8869, (1996), XP002928575.

(Continued)

*Primary Examiner*—James S Ketter
(74) *Attorney, Agent, or Firm*—Nixon Peabody LLP

(57) ABSTRACT

The invention features methods of analyzing the kinetics properties of transfection reactions. Also featured are methods for creating structural promoters which are effectively unregulated by enhancers and repressors. The structural promoters are significantly more active than the native promoter sequences upon which they are based.

36 Claims, 21 Drawing Sheets

OTHER PUBLICATIONS

Escude et al., "Padlock oligonucleotides for duplex DNA based on sequence-specific triple helix formation", Proceedings of the National Academy of Sciences of USA, 96(19), pp. 10603-10607, (Sep. 1999), XP002151269.

Kuhn et al., "Topological links between duplex DNA and a circular DNA single strand", Angewandte Chemie International Edition in English, 38(10), pp. 1446-1449, (1999), XP002462700.

Pan et al., "Initiation of transcription by RNA polymerase II is limited by melting of the promoter DNA in the region immediately upstream of the initiation site", The Journal of Biological Chemistry, 269(48), pp. 30101-30104, (Dec. 1994), XP002462702.

Tantin et al., A heteroduplex template circumvents the energetic requirement for ATP during activated transcription by RNA polymerase II, The Journal of Biological Chemistry, 269(26), pp. 17397-17400, (Jul. 1994), XP002462701.

Supplementary European Search Report based on European Patent Application No. 04760157.0, (Jan. 14, 2008).

* cited by examiner

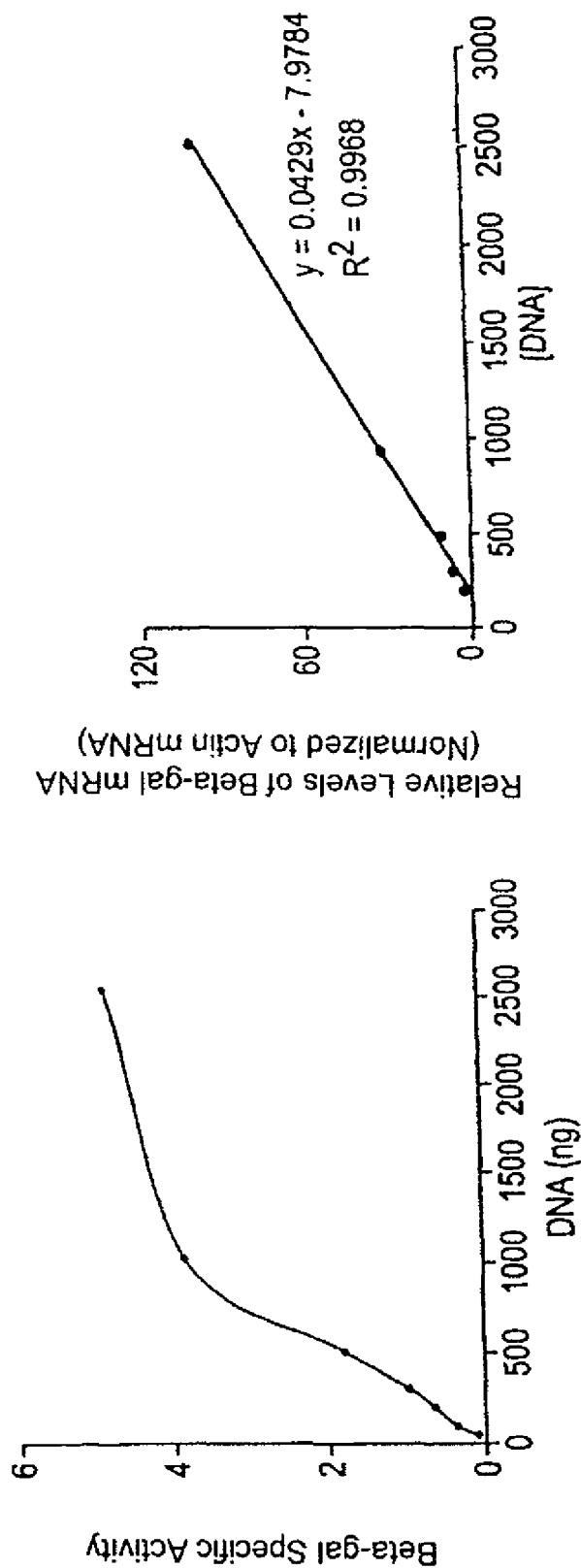

Linear with Concentration of DNA

Linear with Time After Transfection

Comparison of Px & Pe of EF1-alpha

Comparison of Px & Pe of EF1-alpha

Chimeric HCMV/EF-1α Pmin Promoter

HCMV vs. RSV
Matrix Analysis

HCMV vs. RSV
Inverse Plot

Effect of SC Oligos on the Expression of CMV-B,
Lipofectamine Transfection of RD Cells Matrix Plot Effect of SC Oligos on the Expression of CMV-B,
Lipofectamine Transfection of RD Cells Inverse Plot FIG. 15A
FIG. 15B
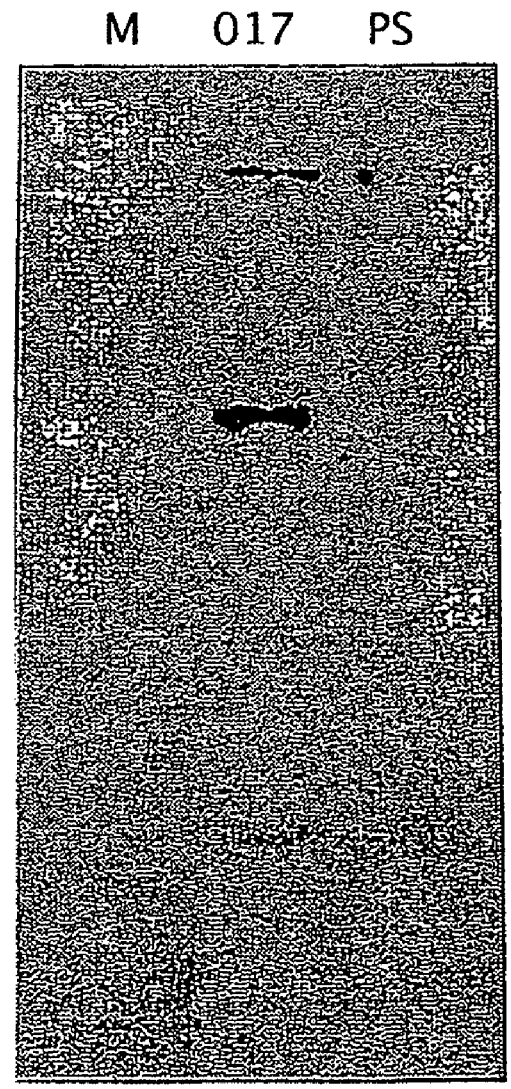

FIG. 17
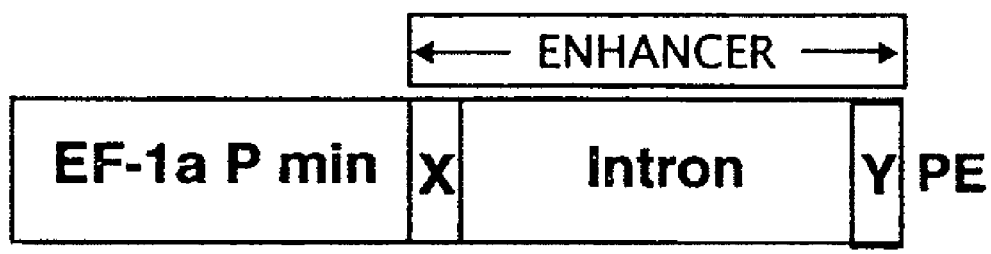
PE
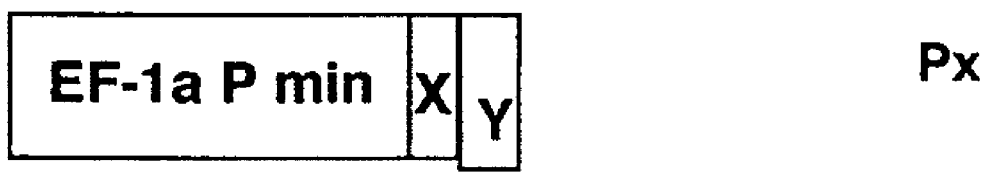
Px
Pmin

TRANSFECTION KINETICS AND STRUCTURAL PROMOTERS

CROSS-REFERENCE TO RELATED APPLICATION

This application is a continuation of U.S. patent application Ser. No. 10/829,747 (filed Apr. 22, 2004) now U.S. Pat. No. 7,527,945, which claims the benefit of U.S. Provisional Application No. 60/464,434 (filed Apr. 22, 2003), and which is a continuation-in-part of Application No. PCT/US2002/33669 (filed Oct. 22, 2002), which claims priority to U.S. Provisional Application No. 60/342,788 (filed Oct. 22, 2001), all of which are hereby incorporated by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: NUCL 012 02US SeqList.txt, date recorded: Nov. 10, 2008, file size 5 kilobytes).

BACKGROUND OF THE INVENTION

Improved methods are needed for measuring the kinetics of transfection of nucleic acid into cells and for measuring promoter activity of the nucleic acid once it is in the cell. Additionally, it would be desirable to have methods for more efficiently expressing RNA or protein molecules of interest within a target cell.

SUMMARY OF THE INVENTION

This invention provides methods for quantifying and describing the kinetics of transfection, a process by which expression of RNA or protein is observed following introduction of DNA into cells. Also provided are permanent and transient forced-open complexes in supercoiled DNA or RNA, as well as methods for creating such complexes. These complexes function as strong transcriptional promoters.

In one aspect, the effect of any expression element on transfection is measured by (i) transfecting a host cell with several (e.g., at least 2, 3, 4, 5, 8, 10, 15, 20, 30, or more) sub-saturating concentrations of a vector comprising the expression element; (ii) measuring the activity of a reporter protein; (iii) measuring the expression of the same reporter protein under the same transfection conditions transfected into control host cells using a vector that is deficient in the expression element under study; and (iv) comparing the expression levels using an inverse plot transformation.

In another aspect, the invention provides a method of expressing an RNA or protein that includes the steps of (i) annealing to a supercoiled or double stranded DNA or RNA an oligonucleotide that is complementary to a sequence upstream from the RNA or protein coding sequence of interest of the supercoiled or double stranded DNA or RNA and (ii) introducing the resulting annealed product into a host cell under conditions that result in expression of the RNA or protein by the host cell. Desirably, the oligonucleotide is annealed to the non-template strand of DNA or RNA. In various embodiments, the host cell may be in cell culture, in a tissue, or in an organism.

In desirable embodiments, the supercoiled DNA or RNA is an expression construct or expression vector. Desirable expression constructs contain a transcriptional promoter operably linked an RNA or protein coding sequence of interest. Desirably, the oligonucleotide forms a heteroduplex with the supercoiled DNA or RNA. In another desirable embodiment, the oligonucleotide is complementary to a naturally occurring or artificially inserted promoter sequence. The oligonucleotide comprises at least 10 nucleotides, desirably at least 20 nucleotides, more desirably at least 30 nucleotides, most desirably at least 40 nucleotides, or even at least 50 nucleotides complementary to the DNA.

In another aspect, the invention provides a composition that includes a DNA expression construct or expression vector, desirably supercoiled, having a torsionally locked single stranded oligonucleotide or padlock oligonucleotide annealed to the DNA upstream from an RNA or protein coding sequence of interest. Desirably, the oligonucleotide forms a heteroduplex with the supercoiled DNA or RNA. In another desirable embodiment, the oligonucleotide is complementary to a naturally occurring or artificially inserted promoter sequence. In various embodiments, the oligonucleotide is a DNA, an RNA, a PNA, or a mixture thereof.

In desirable embodiments of any of the aspects of the invention, the single stranded oligonucleotide comprises at least five contiguous nucleotides at the 5' terminus that are complementary to a first region of the supercoiled DNA or RNA and at least five contiguous nucleotides at the 3' terminus that are complementary to a second region of the supercoiled DNA or RNA that is adjacent to the first region. Desirably, the first and/or second regions of the supercoiled DNA or RNA that are at least 80, 85, 90, 95, or 100% complementary to the 5' or 3' terminus of the single stranded oligonucleotide include at least 10 to 20 nucleotides, more desirably at least 30 nucleotides, most desirably at least 40 nucleotides, or even at least 50 nucleotides or 100 nucleotides. Desirably, at least 5 contiguous nucleotides, more desirably at least 6 contiguous nucleotides at each of the 5' and the 3' termini of the single stranded oligonucleotide are 100% complementary to the corresponding regions of the supercoiled DNA or RNA. In addition to the complementary 5' and 3' sequences, the oligonucleotide desirably has a region linking the 5' and the 3' sequences that is at least as long, and desirably longer, than the total length of the complementary 5' and 3' sequences. Desirably, the linking region consists of nucleotides.

In another aspect, the invention provides a method of expressing an RNA or protein. This method includes (i) providing a single stranded oligonucleotide comprising nucleotides at its 5' terminus (e.g., the first five nucleotides at the 5' terminus) that are complementary to a first region of a supercoiled DNA or RNA expression vector or expression construct and nucleotides at its 3' terminus terminus (e.g., the last five nucleotides at the 3' terminus) that are complementary to a second region of the supercoiled DNA or RNA that is adjacent to the first region; (ii) annealing the oligonucleotide to the supercoiled DNA or RNA such that the 5' and the 3' termini of the oligonucleotide are juxtaposed and base-pair with the first and second regions, respectively, of the supercoiled DNA or RNA; (iii) ligating the 3' terminus of the oligonucleotide to the 5' terminus to form a circular oligonucleotide that is topologically linked to the supercoiled DNA or RNA; and (iv) introducing the resulting DNA or RNA with the topologically linked oligonucleotide into a cell under conditions that allow expression of an RNA or protein encoded by the supercoiled DNA or RNA. The cell may optionally be in cell culture, in a tissue, or in an organism.

In another aspect, the invention features a chimeric HCMV/EF-1 α Pmin promoter. In a related aspect, the invention provides a nucleic acid (e.g., DNA or RNA) expression construct that includes a chimeric HCMV/EF-1 α Pmin promoter operably linked to an RNA or protein coding sequence of interest.

In another aspect, the invention features a composition that includes an HCMV promoter annealed to a torsionally locked oligonucleotide. Desirably, the promoter is operably linked to an RNA or protein coding sequence of interest.

In desirable embodiments of any of the aspects of the invention, the 3' and 5' termini of the single stranded oligonucleotide are each 100% complementary to at least five contiguous nucleotides of the supercoiled DNA or RNA or at least 80, 85, 90, 95, or 100% complementary to at least 6, 10, 15, 20, or 30 (in order of increasing preference) contiguous nucleotides of the supercoiled DNA or RNA. In desirable embodiments, the complementary regions of the supercoiled DNA or RNA are upstream from an RNA or protein coding sequence of interest. Desirably, the regions of complementarity in the supercoiled DNA or RNA are contiguous and are contained within a promoter region (e.g., a TATA and/or CAT box preceding the transcription initiation site of a coding sequence on interest, at least 45 nucleotides prior to the initiating ATG codon of the coding sequence, a region beginning at position −1 relative to the transcription initiation site of the coding sequence, or a region at positions −10 to −70 relative to the transcription initiation site of the coding sequence). The coding sequence of interest in the supercoiled DNA or RNA (e.g., circular, nicked, or linear DNA or RNA) may or may not be operably linked to a promoter. Desirably, the oligonucleotide modulates the expression of the RNA or protein of interest (e.g., increases or decreases expression by at least 2, 3, 5, 10, 15, 20, 30, or 40-fold). In some embodiments, the oligonucleotide has an internal region (e.g., a region linking the 3' and 5' termini that is not base-paired with the supercoiled DNA or RNA) that is less than 50, 40, 30, 20, 10, or 5% complementary to the supercoiled DNA or RNA.

In other embodiments, the oligonucleotide includes one or more modified nucleotides in which the 2' position in the sugar contains a halogen (such as flourine group) or contains an alkoxy group (such as a methoxy group) which increases the half-life of the oligonucleotide in vitro or in vivo compared to the corresponding oligonucleotide in which the corresponding 2' position contains a hydrogen or an hydroxyl group. In yet other embodiments, the oligonucleotide includes one or more linkages between adjacent nucleotides other than a naturally-occurring phosphodiester linkage. Examples of such linkages include phosphoramide, phosphorothioate, and phosphorodithioate linkages. In other embodiments, the oligonucleotide contains sequence or structure that binds regulatory factors, for example, a regulatory sequence (e.g., a transcription factor binding site, a promoter, or enhancer), or the oligonucleotide may contain non-nucleotide entities (e.g., for receptor binding, intracellular targeting, or endosomal disruption).

By "expression element" is meant any feature or sequence of a DNA molecule that affects transcription or translation of a nucleic acid sequence. Examples of expression elements include promoters, enhancers, repressors, polyadenylation sites, and introns. Expression elements that can be assessed using this invention also include protein elements such as transcriptional or translational enzymes, for example, polymerases and transcription factors.

By "expression vector" is meant any double stranded DNA or double stranded RNA designed to transcribe an RNA, e.g., a construct that contains at least one promoter operably linked to a downstream gene or coding region of interest (e.g., a cDNA or genomic DNA fragment that encodes a protein, or any RNA of interest, optionally, e.g., operatively linked to sequence lying outside a coding region, an antisense RNA coding region, a dsRNA coding region, or RNA sequences lying outside a coding region). Transfection or transformation of the expression vector into a recipient cell allows the cell to express RNA or protein encoded by the expression vector. An expression vector may be a genetically engineered plasmid, virus, or artificial chromosome derived from, for example, a bacteriophage, adenovirus, retrovirus, poxvirus, or herpesvirus.

By an "expression construct" is meant any double-stranded DNA or double-stranded RNA designed to transcribe an RNA, e.g., a construct that contains at least one promoter operably linked to a downstream gene or coding region of interest (e.g., a cDNA or genomic DNA fragment that encodes a protein, or any RNA of interest). Transfection or transformation of the expression construct into a recipient cell allows the cell to express RNA or protein encoded by the expression construct. An expression construct may be a genetically engineered plasmid, virus, or artificial chromosome derived from, for example, a bacteriophage, adenovirus, retrovirus, poxvirus, or herpesvirus. An expression construct does not have to be replicable in a living cell, but may be made synthetically.

By "commitment to expression" is meant the likelihood of transcriptional initiation. The commitment to expression is quantified numerically by the $K_m$. Commitment to expression is affected by the affinity of the polymerase for the promoter and by the probability of all of the steps that precede initiation of transcription (i.e., the steps prior to the formation of the first phosphodiester linkage).

By "torsionally locked oligonucleotide" or "padlock oligonucleotide" is meant is a circular nucleic acid (e.g., DNA, RNA, DNA/RNA hybrid, or PNA) or peptide nucleic acid that goes in and out between the two strands of a double-stranded DNA or RNA helix (e.g., circular, linear, or nicked supercoiled DNA or RNA). Padlocks are illustrated in FIG. 12 and described further by Escude et al. (Proc Natl Acad Sci U S A 1999; 96(19):10603-7) and Nilsson et al. (Science. 1994; 265(5181):2085-8), which are both hereby incorporated by reference.

By "non-padlocked oligonucleotide" is meant a single-stranded linear or circular nucleic acid (e.g., DNA, RNA, PNA, or hybrids thereof) annealed as described herein to one strand of a double stranded DNA or RNA helix, but not torsionally locked between the two strands of such DNA or RNA.

By "operably linked" is meant that a nucleic acid molecule and one or more regulatory sequences (e.g., a promoter) are connected in such a way as to permit transcription of the mRNA or permit expression and/or secretion of the product (i.e., a polypeptide) of the nucleic acid molecule when the appropriate molecules are bound to the regulatory sequences.

By a "promoter" is meant a nucleic acid sequence sufficient to direct transcription of a covalently linked nucleic acid molecule. Also included in this definition are those transcription control elements (e.g., enhancers) that are sufficient to render promoter-dependent gene expression controllable in a cell type-specific, tissue-specific, or temporal-specific manner, or that are inducible by external signals or agents; such elements, which are well-known to skilled artisans, may be found in a 5' or 3' region of a gene or within an intron. Desirably a promoter is operably linked to a nucleic acid sequence, for example, a cDNA or a gene in such a way as to permit expression of the nucleic acid sequence.

By "reporter gene" is meant any gene that encodes a product whose expression is detectable and/or able to be quantitated by immunological, chemical, biochemical, or biological assays. A reporter gene product may, for example, have one of the following attributes, without restriction: fluorescence (e.g., green fluorescent protein), enzymatic activity (e.g., β-galactosidase, luciferase, chloramphenicol acetyltransferase), toxicity (e.g., ricin A), or an ability to be specifically bound by an additional molecule (e.g., an unlabeled antibody, followed by a labelled secondary antibody, or biotin, or a detectably labelled antibody). It is understood that any engineered variants of reporter genes that are readily available to one skilled in the art, are also included, without restriction, in the foregoing definition.

By "transformation" or "transfection" is meant any method for introducing foreign molecules into a cell (e.g., a bacterial, yeast, fungal, plant, insect, or animal cell, particularly a vertebrate or mammalian cell). The cell may be in an animal. Lipofection, DEAE-dextran-mediated transfection, microinjection, protoplast fusion, calcium phosphate precipitation, viral or retroviral delivery, electroporation, and biolistic transformation are just a few of the transformation/transfection methods known to those skilled in the art. The nucleic acid may be, for example, naked RNA or DNA or a local anesthetic complexed to RNA or DNA. Other standard transformation/transfection methods and other RNA and/or DNA delivery agents (e.g., a cationic lipid, liposome, or bupivacaine) are described in WO 00/63364, filed Apr. 19, 2000 (see, for example, pages 18-26). Commercially available kits can also be used to deliver RNA or DNA to a cell (e.g., Transmessenger Kit from Qiagen, an RNA kit from Xeragon Inc., and an RNA kit from DNA Engine Inc. (Seattle, Wash.)).

BRIEF DESCRIPTION OF THE DRAWINGS

FIGS. 2A and 2B are a series of graphs showing the β-gal enzymatic activity and mRNA levels in RD cells following transfection with varying amounts of vector DNA. The mRNA was quantified using a Phosphorimager (Molecular Dynamics, Sunnyvale, Calif.) of Northern blots hybridized using a radioactive β-gal or SEAP specific DNA probe. Northern blotting was performed according to the methods described in Sambrook et al., Cold Spring Harbor Press, Plainview, N.Y. (1989). The mRNA was also quantified using a quantitative RT-PCR method using oligonucleotides designed to specifically prime and amplify target mRNAs.

FIGS. 15A and 15B depict an electrophoretic separation of vector DNA following incubation and enzymatic ligation with a $^{32}$P-labeled "padlock" oligonucleotide. FIG. 15 A is a picture of an ethidium bromide stained gel, and FIG. 15 B is a picture of an autoradiogram (Phoshorimager, Molecular Dynamics, Sunnyvale, Calif.) of the same gel. The three lanes in the gels are DNA markers (M), a Betagal plasmid preparation that contains linear, open circular, and supercoiled forms (017), and all three plasmid forms of pShooter (Invitrogen, Carlsbad, Calif.) as control (PS) (a plasmid without betagal sequences). FIG. 15B has a radioactive band associated only with the SC form of the betagal (017) plasmid. No radioactivity is associated with the control pshooter plasmid (PS) or with the marker DNA (M). The padlock sequences were designed to base-pair with the betagal sequences, and the padlocking reactions were carried out against mixed plasmid forms of both betagal (017) and pShooter (PS) preparations. The figure demonstrates specificity to supercoiled DNA and further proves that the supercoiled DNA "breathes," and that an oligonucleotide can indeed invade and hybridize to the single stranded loops generated.

FIG. 17 depicts the various EF-1α Promoter constructs described herein. PE is comprised of a promoter element, EF-1α Pmin, and an enhancer. The enhancer is comprised of an intron and two flanking exons, x and y. Px is comprised of the promoter element, EF-1α Pmin, and x and y are derived from the enhancer element. Pmin is the minimal promoter element, EF-1α Pmin.

DETAILED DESCRIPTION

Figure 1:
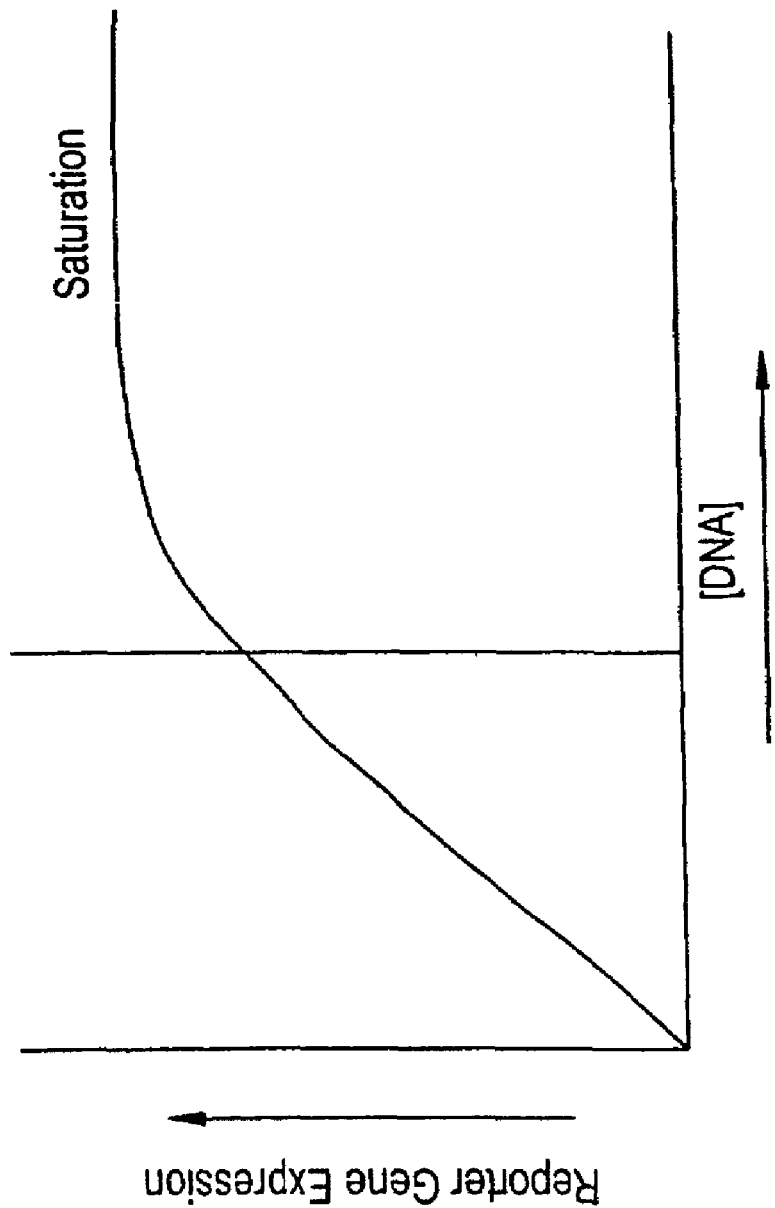
FIG. 1 is a graph of reporter gene expression as a function of the plasmid DNA concentration used in the transfection procedure. The concentration of reporter plasmid DNA expressing beta-galactosidase (β-gal) or secreted alkaline phosphatase (SEAP) was varied as indicated on the X-axis, from 50 ng to 2.5 micrograms. The total DNA concentration was kept constant at 2.5 micrograms by adding a promoterless luciferase plasmid as filler DNA. The DNA was then complexed with Lipofectamine™ to ensure that similar Lipofectamine complexes were applied to the cells, and these complexes were added to RD cells. The transfection process was as described in Example 5C. The cells were lysed to determine β-gal activity or culture supernatants were used to measure SEAP activity. Cells were lysed as described herein. β-gal activity was measured as described in *Molecular Cloning, A Laboratory Manual,* 2nd Edition. Sambrook, J., Fritsch, E. F. and Maniatis, T.; Cold Spring Harbor Press, Plainview, N.Y. (1989); however, the assay was carried out kinetically as described herein. The initial velocities obtained as described herein were plotted as a function of varying amounts of reporter DNA in the transfection mixes.
Figure 3A:
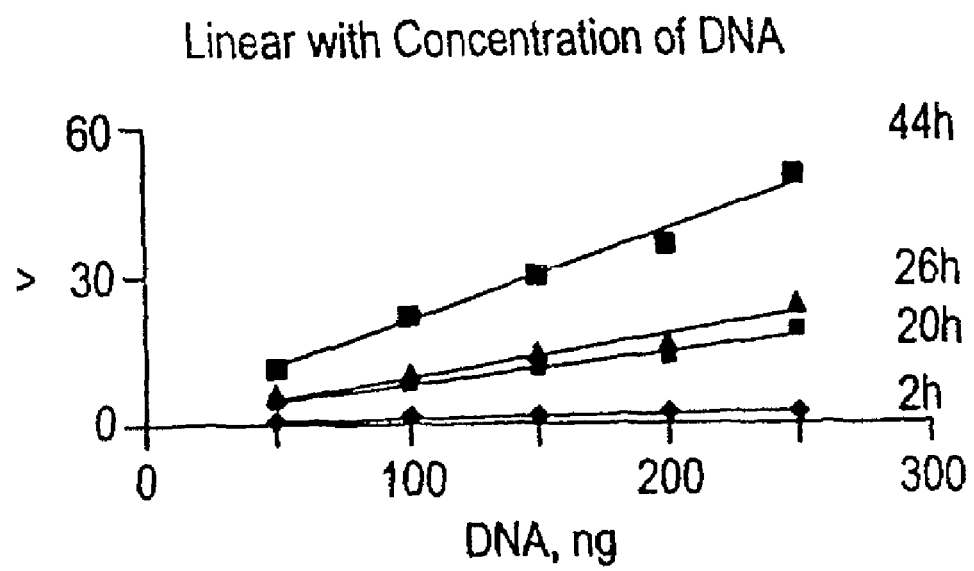
FIGS. 3A-3D are a series of graphs showing that the transfection process (transfection) is amenable to steady state kinetic analysis. To enable steady state kinetic analysis, the amount of product formed has to be linear with respect to the amount of cells in the transfection mixture, linear with respect to time following transfection, and exhibit a Micaelis-Menten substrate (DNA) saturation profile with linearity at DNA concentrations below the $K_m$. Transfections were carried out as described previously. Cell numbers and the amounts of DNA were varied as indicated.
Figure 3B:
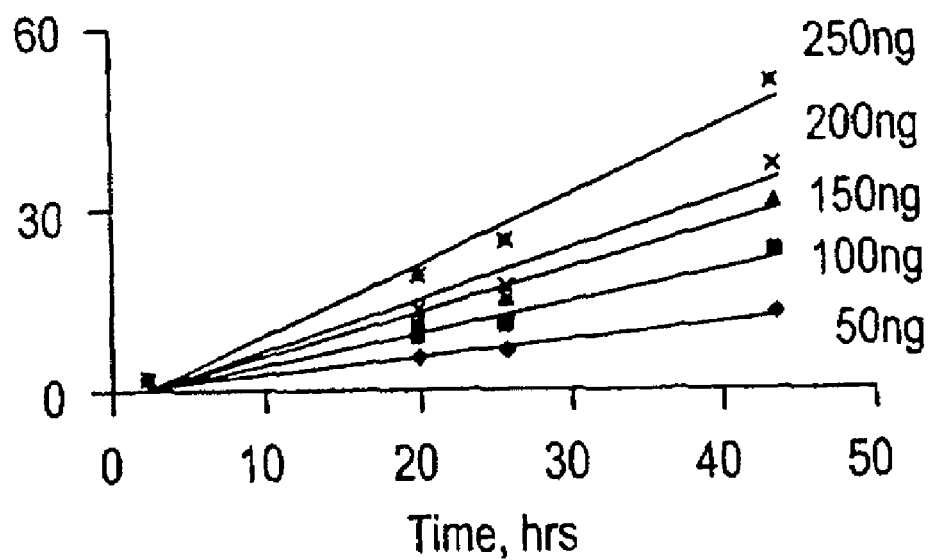
Figure 3C:
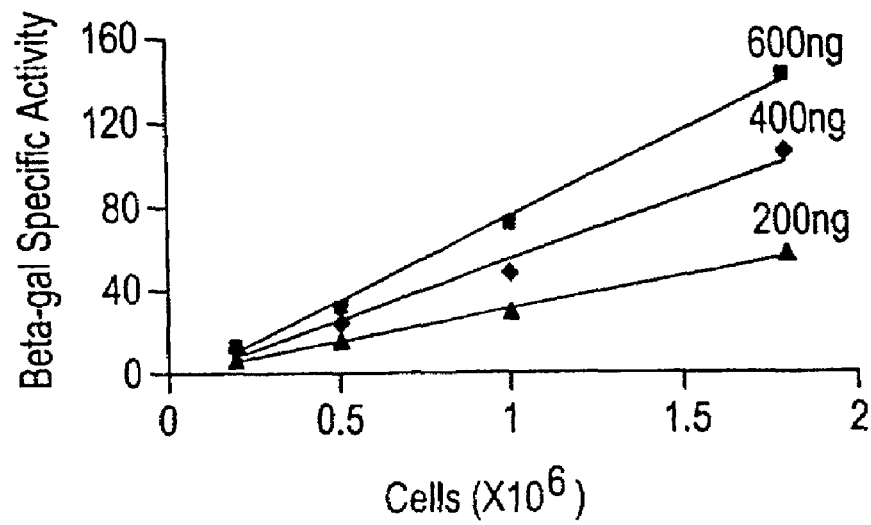
Figure 3D:
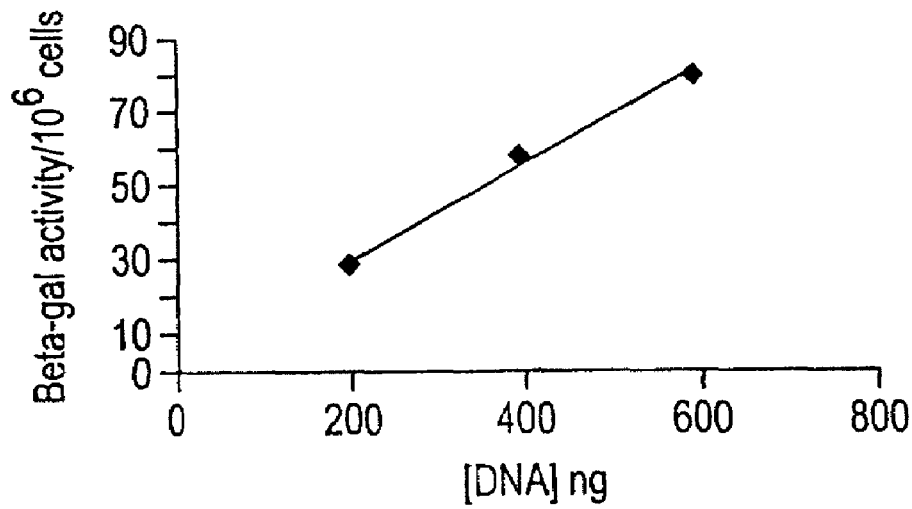

Transfection of DNA into cells is the primary step in the analysis of gene expression. Quantitative analysis of gene expression requires that transfection efficiency differences do not compromise the comparative analysis of expression elements. The present invention relates to methods for analyzing the relative expression of transfection constructs. The methods are based on our discovery that transfection is a saturable process, and that the expression profile of a reporter construct is amenable to steady state kinetic analysis.

In a one aspect of the invention, using the analytical methods, we have re-defined gene promoters by structural, rather than sequence, criteria. Based on the discovery of the structural characteristics of promoters, we provide a strategy for creating super promoters that are significantly stronger than the native promoters on which they are based. Additionally, this strategy can be used to create a functional promoter site at genetic sites that do not encode any expression elements.

Another aspect of the invention provides improved artificial promoters created by linking sequences demonstrated through the analytical methods of the invention to have desirable kinetic characteristics.

In another aspect, the invention provides DNA expression constructs and expression vectors, desirably supercoiled, having a torsionally locked single stranded oligonucleotide or padlock oligonucleotide annealed to the DNA upstream from an RNA or protein coding sequence of interest. Also provided are DNA expression constructs and expression vectors, desirably supercoiled, having a single stranded oligonucleotide annealed to a DNA sequence upstream from the protein or RNA coding sequence of interest. In desirable embodiments, the single stranded oligonucleotide is annealed to a naturally occurring or artificially inserted promoter sequence.

Transfection Kinetics

The expression of various genetic elements can be described using the standard kinetic constants, $V_{max}$ and $K_m$. The $K_m$ is a measure of the commitment to expression of a genetic element. The lower the $K_m$, the greater the commitment. The $K_m$ therefore defines the amount of DNA expression construct required to be effective. Low $K_m$ indicates that the expression machinery can sense even smaller quantities of internalized DNA as compared to the amounts of sequences that have higher $K_m$. Delivery of DNA expression vectors is inefficient in vivo. Therefore, it is desirable to include elements of a promoter that has an exceedingly low $K_m$. The $V_{max}$ is a measure of the relative expression potential of the element at infinite (unlimited) concentrations of template DNA (expression vector). $K_m$ and $V_{max}$ do not co-segregate with the same DNA sequences, and are predicted to be associated with definable DNA sequences. Therefore, it is possible to create artificial promoters by using elements of low $K_m$ and high $V_{max}$. In some embodiments, a promoter is created by combining a region associated with a low $K_m$ with a region associated with a high $V_{max}$.

Cell culture transfection typically results in the cellular uptake of hundreds of DNA molecules per cell, and is a process that can be saturated. At transfection saturation, protein expression levels plateau such that further increases of transfecting DNA do not result in proportional increases in transgene expression. At saturation, at least one of the components of the transfection process is limiting. Accordingly, meaningful and accurate measurements of relative expression levels must be taken at sub-saturating concentrations. The sub-saturating concentrations are often orders of magnitude smaller than those used for in vitro transfection, and may be more applicable for in vivo applications.

We have invented a matrix transfection assay that measures protein expression in the linear range of transfection, as a true measure of the differences among expression elements. The assay also allows discrimination of transfection efficiency effects. Using this assay, we have discovered that: (1) transfection is saturable; (2) saturation of transfection occurs at a post-transcriptional step; and (3) co-transfection is not a reliable indicator of transfection efficiency when performed under saturating conditions.

Example 1

Measuring the Kinetics of Transfection

Transfections were performed using cationic lipid (Lipofectamine) complexed DNA in human Rhabdomyosarcoma (RD) cells. Amounts of transfected reporter gene plasmid in transfection mixes ranged from 50 ng to 2.5 µg/transfection. The total amount of DNA per transfection was held constant at 2.5 µg by adding a promoterless control plasmid to each transfection reaction.

A variety of reporter plasmids were used. Plasmids were designed to express β-galactosidase or human secreted alkaline phosphatase (SEAP), and contained various promoter elements including the HCMV, SCMV (Chang et al., J. of Virology, 64: pp 264-277, 1990;) HCMVm (e.g., a HCMV promoter with a gfi transcription factor binding sequence deleted), Zweidler-McKay et al., Molecular and Cellular Biology, 16: pp 4024-4034, 1996), and elongation factor 1 alpha (EF-1α) minimal and complete promoters (WO 02/50264A2). Additionally, intron-containing and intronless vectors were compared.

Enzyme Expression Analysis

Beta-galactosidase (βgal) activity was measured in the lysates of transfected cells using a calorimetric kinetic enzyme assay, and normalized to total cellular protein. SEAP activity was measured in the media of transfected cells. Expression is plotted as the initial velocity of the reaction for each DNA concentration tested. Enzymatic activity was measured at several time points during the reaction. The measurements of the reaction over time were plotted. Slope of the linear portion of the reaction curve is the initial velocity rate utilized in the transfection plots. The initial velocity of the enzymatic reactions is directly proportional to the amount of the enzyme present. Enzymatic assays were performed at 1, 2, and 4 days post-transfection. All vectors, regardless of cell type, resulted in transfection saturation (FIG. 1). For different combinations of vector and cells, saturation occurred at different amounts of DNA in the transfection mixture. Saturation occurred at expression vector levels ranging from 200 ng-1 µg per $6-7 \times 10^5$ cells.

RNA Analysis

Total RNA was isolated from cells using the StrataPrep Total RNA Miniprep Kit (Stratagene). Three micrograms of total RNA was run on a 1.2% agarose-formaldehyde gel, transferred to Zeta-probe membrane (Bio-Rad), and probed with β-gal sequences. After initial hybridization, the membrane was stripped and probed for actin RNA. Probes were $^{32}$P-labeled using random primed synthesis. The resulting signals were visualized and quantitated by phosphorimager analysis. Relative RNA values were obtained by normalizing β-gal RNA to actin RNA.

Experiment #1

FIG. 2 shows representative results of β-gal enzymatic activity and mRNA level, as a function of vector DNA concentration. Experiments were performed in duplicate. β-gal expression was found to be linear up to 1 µg of transfected reporter plasmid, after which, expression levels became saturated. β-gal RNA levels were linear over the entire range of DNA concentration used. Replicates exhibited less than 5% variation. Together, these data show that saturation of transfection (protein expression) occurs at a post-transcriptional step.

Sub-saturating concentrations of β-gal vector DNA were used to investigate other kinetic properties of the transcription system. FIG. 3 shows that β-gal activity increases linearly, under sub-saturating conditions, with increasing time after transfection (A and B), with cell density (C).

Experiment #2

Sub-saturating amounts of β-gal reporter plasmid (200 ng) were co-transfected with a super-saturating amount of a second plasmid (2.3 µg). The second plasmid was either HCMV-HSVgD (expresses a protein product), HCMV-HPVL1 (expresses mRNA that is transcribed, transported to the cytoplasm, but not translated), or pLUC (promoterless plasmid that is not transcribed). The HCMV sequence has Genbank Accession number X 03922.

β-gal protein and mRNA were measured and normalized as previously described. The lowest expression of protein and RNA was assigned an arbitrary value of one, and the ratio of β-gal protein:RNA was compared.

Approximately equal amounts of mRNA are made by the HCMV-HSVgD and the HCMV-HPVL1 plasmids, as measured by RT-PCR. There was no difference in the amount of β-gal protein per unit β-gal RNA in cells co-transfected with non-protein coding plasmids (HCMV-HPVL1) compared to cells transfected without a competing plasmid (HCMV-HSVgD). However, in cells co-transfected with plasmids that directed the synthesis of a protein (HCMV-HSVgD), 14-18 fold less β-gal protein per unit β-gal RNA was produced (compare pLUC or HCMV-HPVL1 to HCMV-HSVgD). RNA levels proportionately increase with DNA transfected, while protein levels do not. Moreover, the expression of protein is competed with higher concentrations of only protein-expressing plasmids (as opposed to plasmids that express mRNA which is not translated). This result indicates that the limiting elements of expression involve post-transcriptional steps and that saturation occurs post-transcriptionally.

TABLE 1

Competition Experiment to Define Saturation

| Construct | Expression Block | β-gal protein level | β-gal RNA level | β-gal protein:RNA |
|---|---|---|---|---|
| HCMV-HSVgD | no block | 1 | 1.8 | 0.56 |
| HCMV-HPVL1 | translation | 8-10 | 1 | 8-10 |
| pLUC | transcription | 8-10 | 1 | 8-10 |

Experiment #3

Figures 4A, 4B:
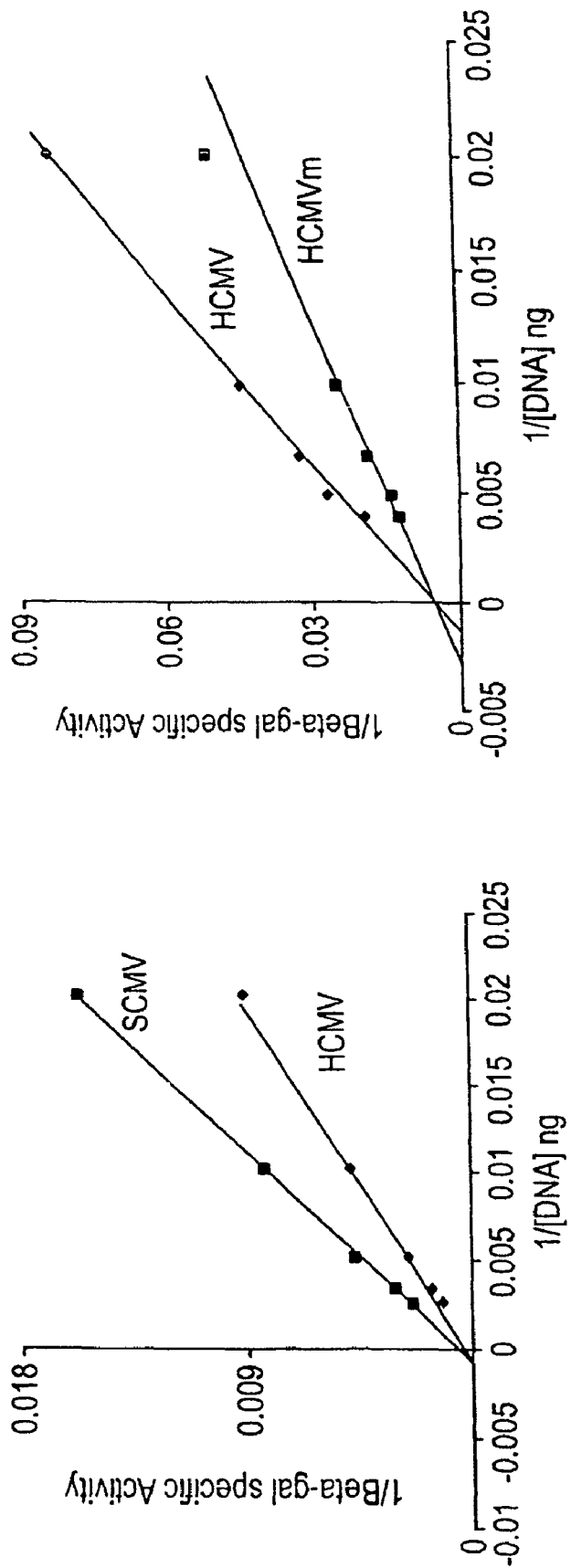
FIGS. 4A and 4B are a series of graphs comparing β-gal activity following transfection under sub-saturating conditions in RD cells. β-gal is under the control of either the HCMV, SCMV, or HCMVm promoter. The plots are of inverse values for initial velocity (Y-axis) and for substrate (X-axis) in Lineweaver-Burk format.

Kinetic constants of two different promoter constructs were compared. FIG. 4 is an inverse plot of initial velocities as a function of DNA concentration (Lineweaver-Burk plot). The $V_{max}$ is derived from the Y-axis intercept, and the $K_m$ from the X-axis intercept. The HCMV promoter, when compared with the SCMV promoter (Chang et al., J. of Virology, 64: pp 264-277, 1990) demonstrates differences in initial velocity rates. Therefore, even at saturating substrate concentrations, these two promoters are predicted to have different levels of activity (HCMV>SCMV). The similarity of $K_m$ values suggests similar commitments to catalysis.

When the HCMV promoter is compared with the HCMVm version harboring a mutation in the gfi box (transcriptional repressor site) (Zweidler-McKay et al., Molecular and Cellular Biology, 16: pp 4024-4034, 1996) the two promoters have significant differences in their initial velocity rates, but at saturating concentrations of DNA, they are predicted to have similar velocities ($V_{max}$). The promoters do, however, have different $K_m$ values, with the mutant showing a higher commitment to catalysis (lower $K_m$). $K_m$ differences reflect differences in events that lead to transcription initiation resulting from differences in affinity for the transcription machinery. $V_{max}$ differences reflect, in most instances, the activity following transfection with infinite DNA concentrations.

Experiment #4

Figure 5:
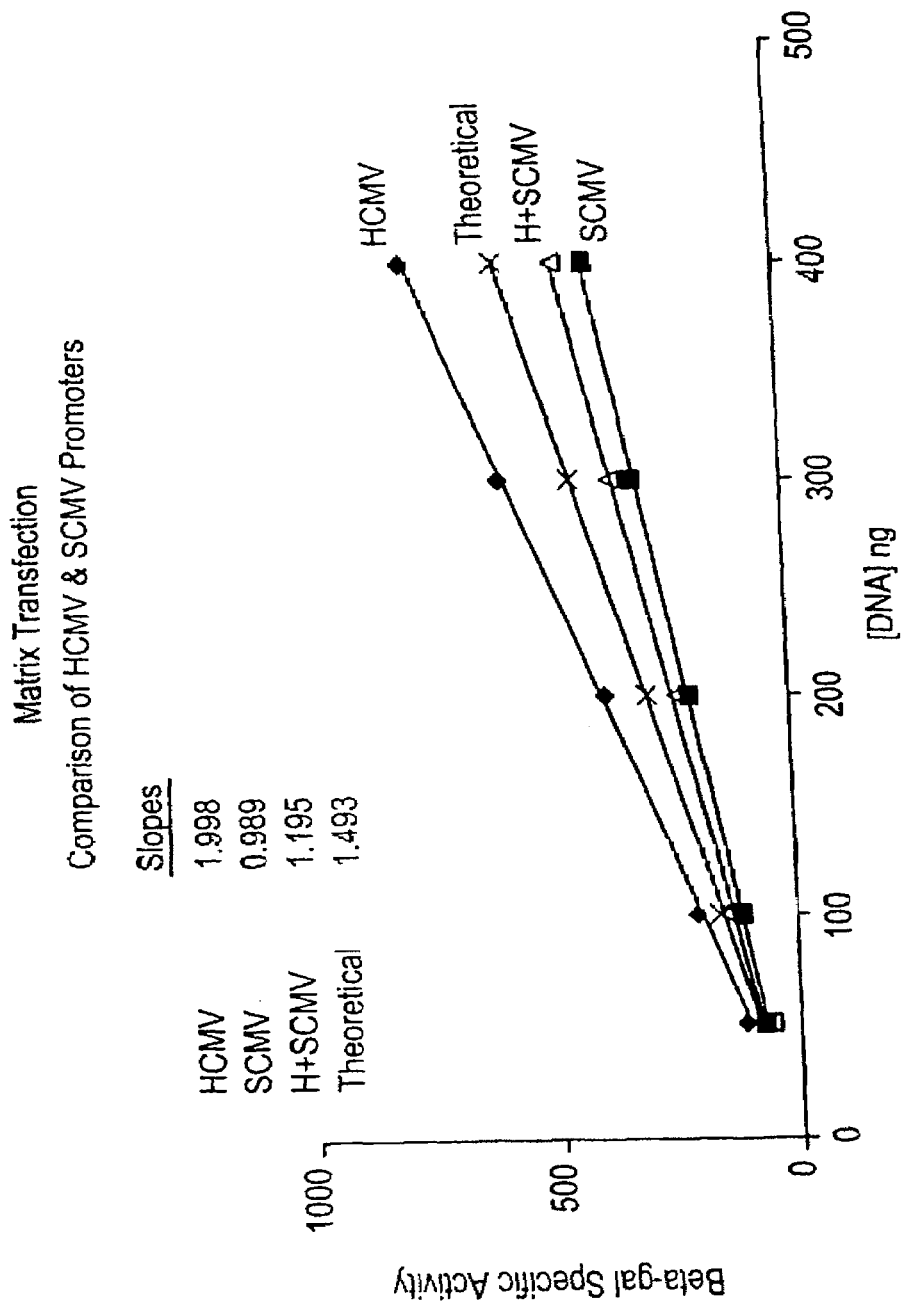
FIG. 5 is a graph comparing the β-gal activity in RD cells following transfection with vectors containing either an HCMV or SCMV promoter. Single construct transfections are compared to mixed transfections as described herein.

The relative activity of the HCMV promoter and the SCMV promoter in RD cells was compared (FIG. 5). Transfection was performed in the linear range of DNA concentration, and enzyme activity results were corrected from transfection efficiency differences. The HCMV and SCMV β-gal expression vectors were identical to each other in all respects with the exception of the promoter sequences.

RD cells were transfected with the HCMV β-gal reporter plasmid, the SCMV β-gal reporter plasmid, or a mixture of the two plasmids (H+SCMV). For single plasmid transfections, reporter plasmid DNA amounts were 50-400 ng. Total DNA per transfection was held constant at 2.5 µg by adding a promoterless control plasmid. In order to control for transfection efficiencies and to be able to compare transfection values of different constructs at different amounts of DNA in the transfection mixture, the two plasmids were mixed in equal proportions and used in the transfection. For the mixed plasmid transfection (H+SCMV), equal amounts of each plasmid were used (e.g., the 50 ng transfection contained 25 ng of each plasmid). In the linear range of transfection, at DNA levels below the $K_m$ the plot of initial velocity over DNA added to cells is predicted to be linear. The slope of the line derived for the mixture is predicted to be an average of the slopes of the two lines derived for HCMV and SCMV, if transfection efficiencies were similar.

The relative expression level of HCMV to SCMV (2.022) is derived from the ratio of the slopes (1.998÷0.988). The differences, however, may reflect variations in transfection efficiencies rather than true differences in relative expression levels. Variations in transfection efficiency were measured in a mixed transfection.

If no differences in transfection efficiency exist between the HCMV and SCMV preparations, a mixed plasmid transfection will yield a theoretical slope of 1.493. The presence of inhibitors or enhancers of transfection in one of the preparations would alter the theoretical slope. In fact, the mixed transfection generated a lesser slope (1.195) than the theoretical slope, indicating that the reduced expression of SCMV was, in part, a result of differences in transfection efficiency. The level of repression caused by transfection inhibition (caused by elements of transcription prior to the entry of DNA into cells) can be calculated by dividing the theoretical slope by the experimentally derived slope of H+SCMV; 1.255 in this experiment. Expression of SCMV is then corrected by multiplying the experimental value (0.988) by the repression factor (1.255). The true relative activity is then determined by dividing HCMV activity by the corrected SCMV activity.

Experiment #5

Figure 6A:
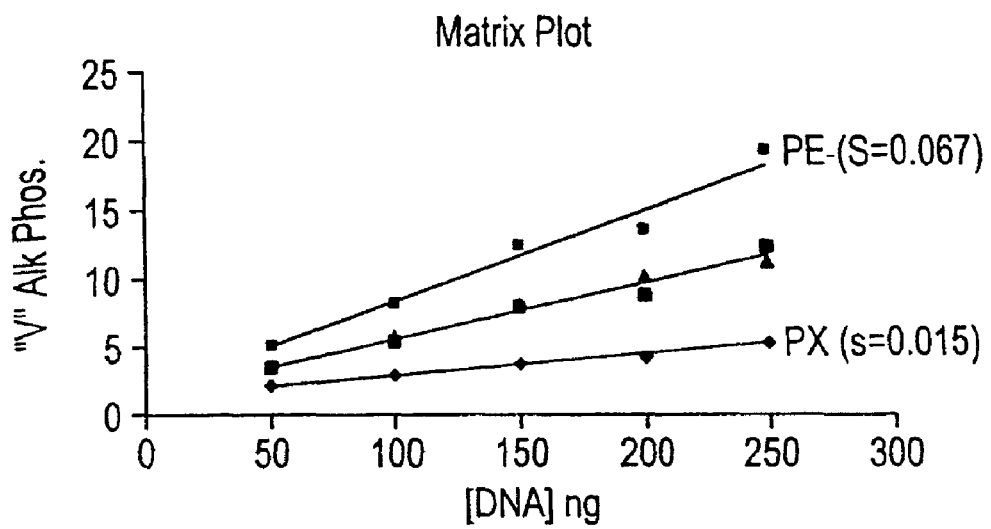
FIGS. 6A and 6B are graphs comparing the effects of inclusion or deletion of the enhancer element of EF-1α promoter.
Figure 6B:
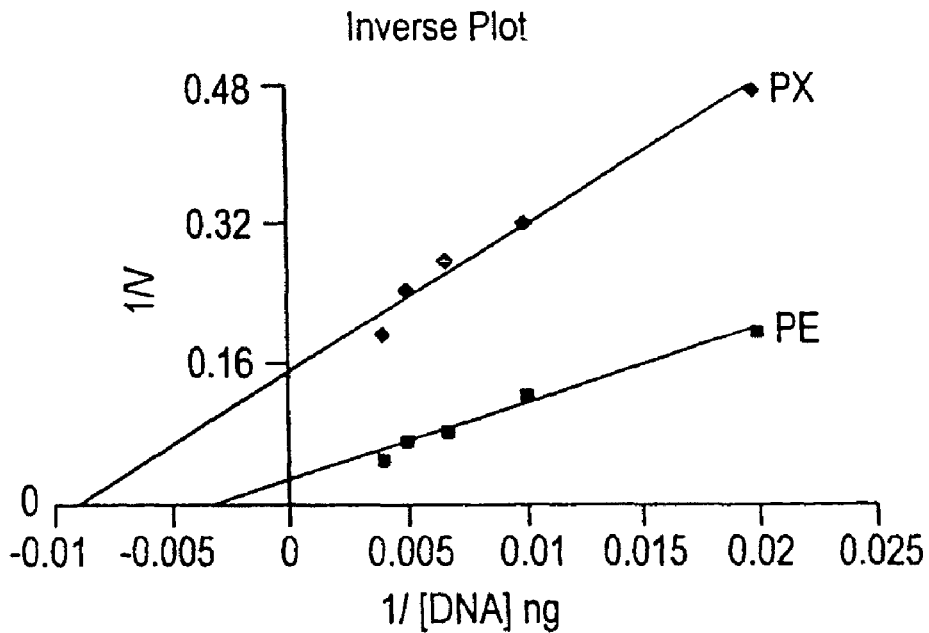

A similar kinetic analysis was performed to study the effects of other promoters and other genetic elements. FIG. 6 shows the effect of the enhancer element on the elongation factor alpha promoter (EF-1α promoter). Publication WO 02/50264, which is incorporated herein by reference, contains the EF-1a promoter (SEQ ID No. 1).

Promoter-Intronless "Enhancer" Sequence: Ef-1a Px Construct

A promoter sequence was constructed with the following sequences: a minimal EF-1a promoter (Pmin) (nucleotides 1-204 of SEQ ID NO: 1), linked to a sequence containing the 5' exon of the native enhancer (nucleotides 205-238 of SEQ ID NO: 1), which is linked to a sequence containing the 3' exon of the native "enhancer" (nucleotides 1160-1170 of SEQ ID NO: 1) but lacks the intron sequence of the native "enhancer" located between the two exons. This synthetic sequence contains nucleotides 1-238 immediately fused to nucleotides 1160-1170 of SEQ ID NO: 1. This construct is referred to as the Ef-1a Px construct. When this sequence was employed as the promoter in the above-described plasmid construct, it provided a 2-fold increase in expression relative to the minimal promoter plasmid in expression assays. The expression was, however, lower than that obtained using the plasmid construct containing the entire native EF-1a promoter-"enhancer" which is referred to herein as the EF-1a PE construct. The inverse plot demonstrates that the enhancer element reduces the commitment of the promoter to transcription (increases $K_m$), but increases the maximal rate at which the gene is transcribed (increases $V_{max}$). A schematic diagram of the EF-1a promoter organization and the constructs used in the studies described herein are shown in FIG. 17.

Figure 7A:
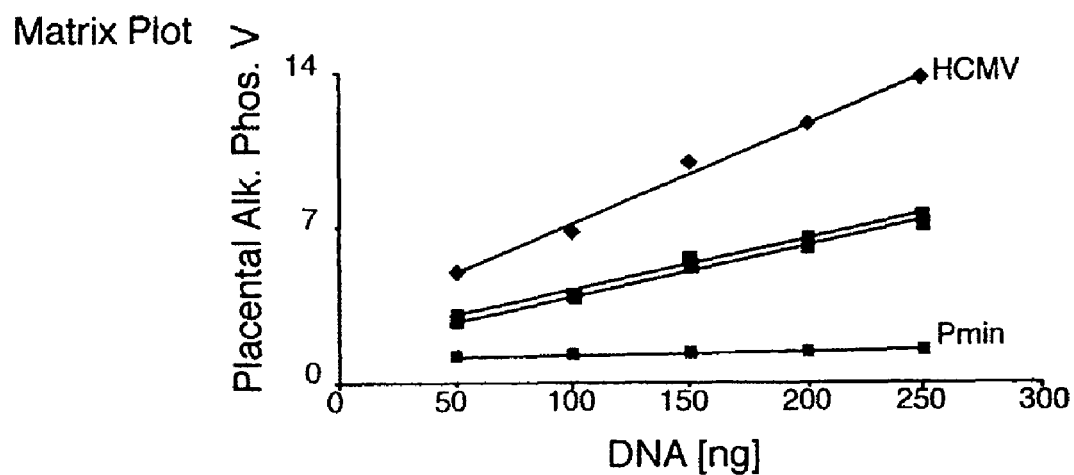
FIGS. 7A and 7B are graphs comparing the effects of the HCMV and EF1α Pmin promoters on β-gal expression in RD cells after transfection using sub-saturating conditions. Saturation of transfection results from limiting amounts of one or more of the components or steps in the transfection machinery (e.g., DNA uptake, nuclear transport of DNA, transcription factors, polymerase, triphosphoribonucleosides, splicing, capping, polyadenylation, transport of mRNA to the cytoplasm, ribosome binding, translation, protein folding, translocation of the protein into the ER).
Figure 7B:
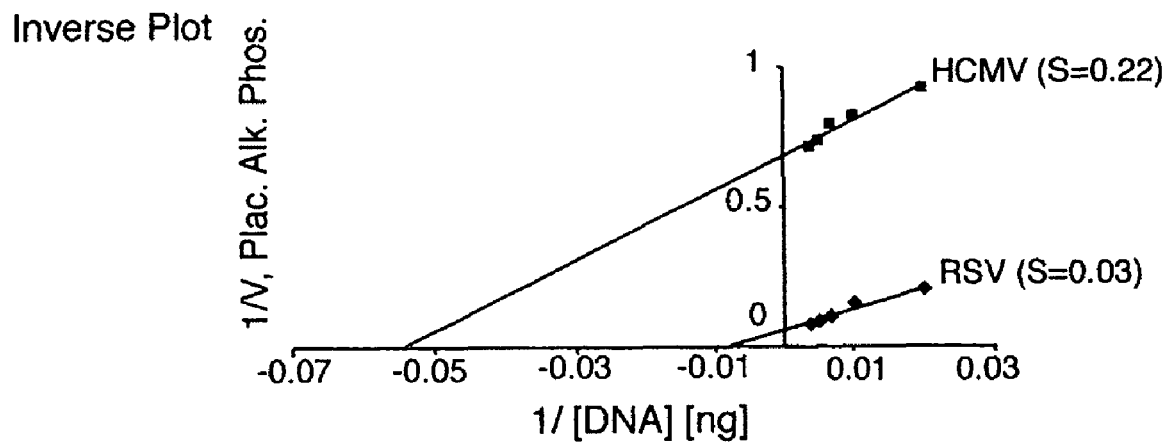

Another experiment (FIG. 7) compares the kinetics of the HCMV promoter with the EF-1α Pmin promoter construct. The inverse plot demonstrates that the HCMV promoter has a relatively lower commitment to transcription. Therefore, the HCMV promoter would not be expected to be active at a low copy number and is not predicted to be useful under sub-saturating transfection (DNA uptake) conditions. However, the EF-1α Pmin is predicted to be efficient in achieving commitment at low transfection efficiencies (plasmid DNA uptake). The HCMV promoter demonstrates a very high $V_{max}$—greater than 30 fold over EF-1α Pmin. To achieve high level expression at very low DNA uptake as would be needed for gene therapy, DNA vaccine, and RNAi applications, it would be useful to replace the sequence element of HCMV that contributes to the high $K_m$ with the EF-1 alpha Pmin sequences, as described in Example 2 below.

Figure 9A:
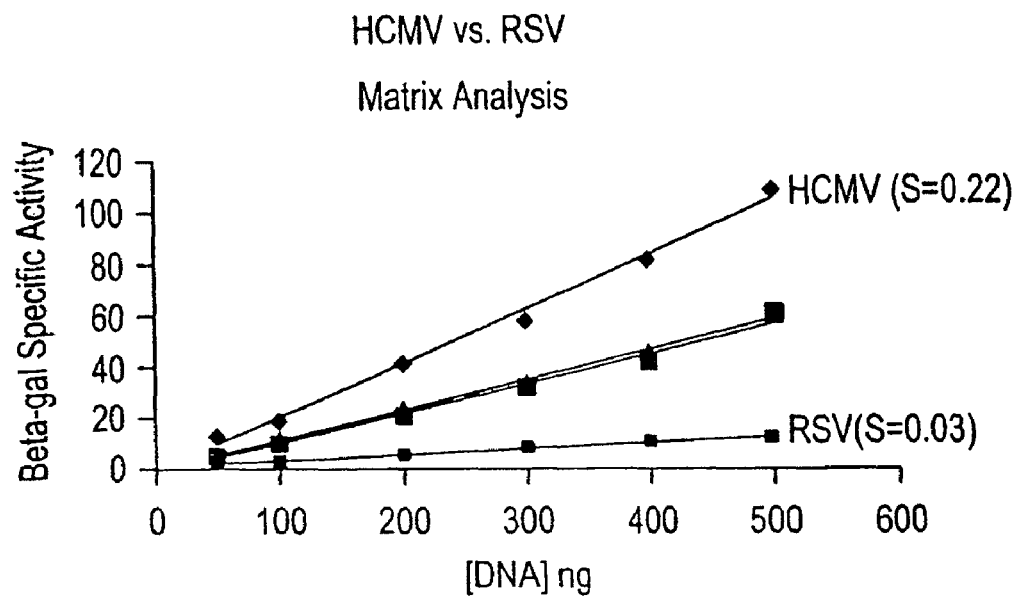
FIGS. 9A and 9B are graphs comparing the effects of the HCMV and RSV promoters on β-gal expression in RD cells after transfection using sub-saturating conditions.
Figure 9B:
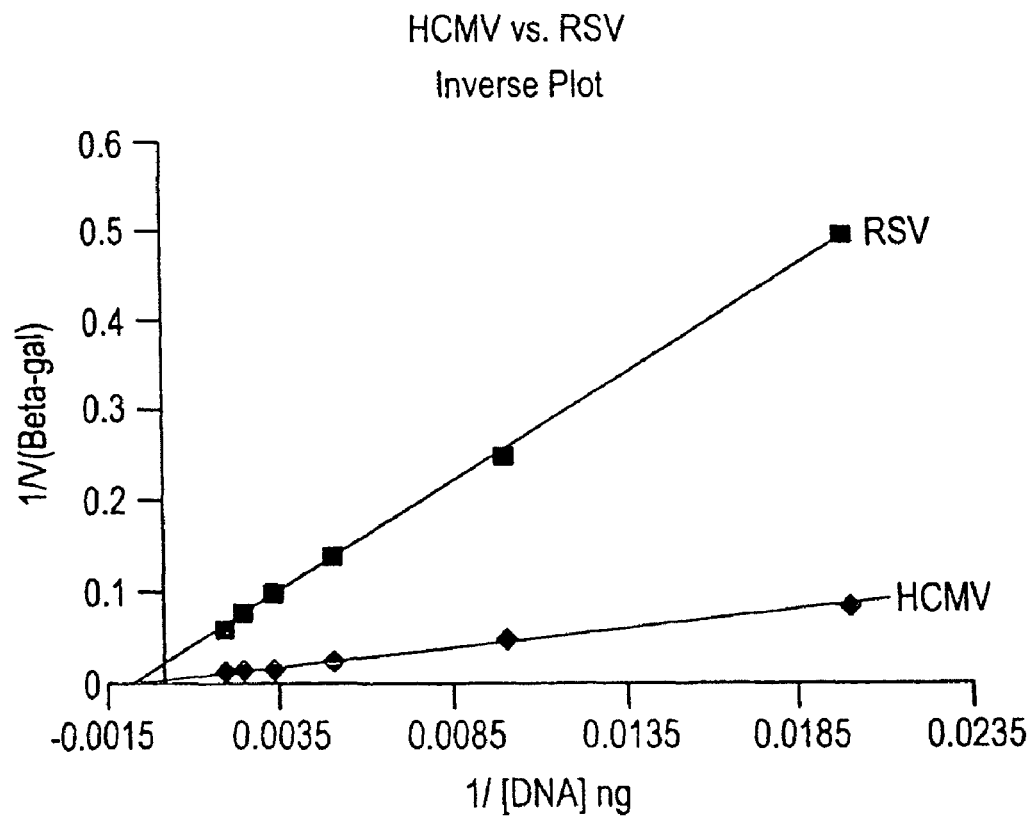

FIGS. 9A and 9B compare the kinetics of the HCMV promoter to the Rous Sarcoma virus promoter (RSV). Both promoters are approximately equally committed to transcription ($K_m$); however, the HCMV promoter results in higher expression levels at any concentration of transfection DNA ($V_{max}$).

The experiments shown in FIGS. 6A, 6B, 7A, 7B, 9A, and 9B were controlled for differences in transfection efficiency. In all cases, the mixture of the two plasmids resulted in β-gal activity intermediate between the activity observed with each vector alone. Therefore, no DNA uptake efficiency correction was necessary.

Mapping Promoter Elements Using a Genetic Approach

The sequence elements that contribute to $K_m$ and $V_{max}$ effects can be mapped by random mutation either in vitro (e.g., by PCR based mutagenesis, sequence shuffling, or mutagenizing), in vivo in bacteria or eukaryotic cells with single or multiple copy plasmids, or using integrated sequences (e.g., retroviruses, random integration, Cre-Lox). Once identified, the sequence elements can be spliced together to get the desired promoter effect, such as a promoter with a low $K_m$ and a high $V_{max}$.

This kinetic testing methodology is not limited to promoter assessment. These techniques can be used to measure the effects of any transcriptional or translational control elements, promoters being only one example. These methods are also applicable for the optimization of transfection conditions.

Example 2

Construction and Function of a Chimeric HCMV/EF-1α Min Promoter (Chimeric HCMV/EF-1α Pmin Promoter)

Generation of Constructs

The minimal promoter of the human elongation factor-1 alpha promoter-enhancer (EF-1α Pmin, WO 02/50264) is used to create a chimeric promoter by joining this EF-1α minimal promoter to sequences in the HCMV promoter. The sequence of the EF-1α minimal promoter, nucleotides 1-204, is as follows:

```
                                            (SEQ ID NO: 2)
   cgtgaggctc cggtgcccgt cagtgggcag agcgcacatc gcccacagtc cccgagaagt tgggggggagg ggtcggcaat tgaaccggtg cctagagaag gtggcgcggg gtaaactggg aaagtgatgt cgtgtactgg ctccgccttt ttcccgaggg tgggggagaa ccgtatataa gtgcagtagt cgccgtgaac
   0
   gttc.
```

Figure 8:
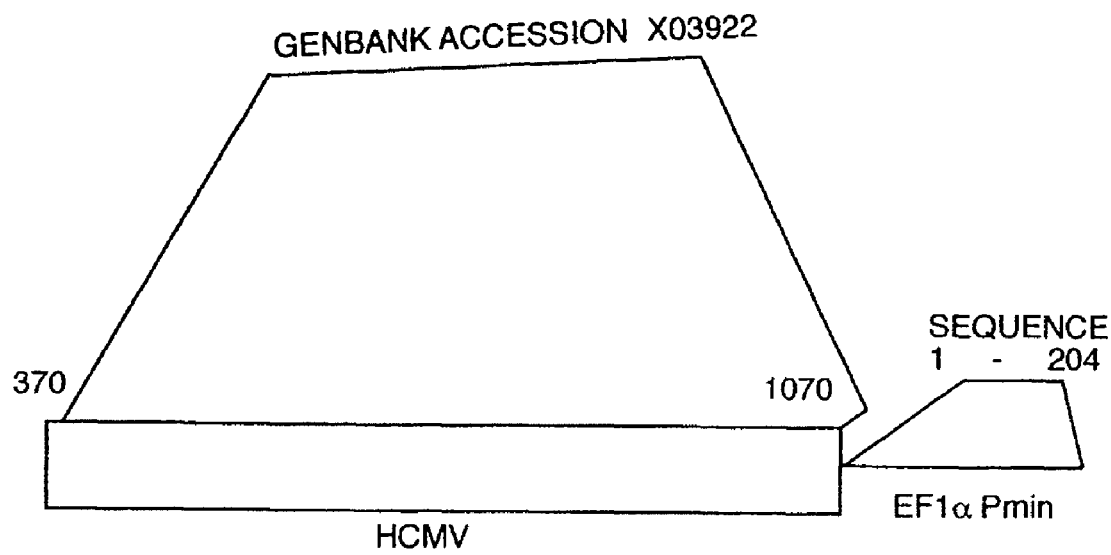
FIG. 8 is a schematic diagram of the chimeric HCMV/EF-1α Pmin promoter described in Example 2. The EF-1α Pmin promoter replaces the 3' terminal 71 base-pairs of the HCMV promoter and is adjacent to coordinate 1070 of the HCMV promoter according to GenBank Accession # X03922.

In this particular example, the 3' terminal 71 base-pairs containing the TATA and CAT boxes are first deleted from the HCMV immediate early promoter (GenBank accession # X 03922). The EF-1α min promoter element replaces these deleted HCMV sequences as depicted in FIG. 8. Cloning of the EF-1 α Pmin promoter element is described in WO02/50264. For cloning the HCMV promoter containing the 71 base-pair deletion, the following strategy is employed. The 5' portion of the human cytomegalovirus (HCMV) immediate early promoter (nucleotides 370-1070 of Genbank accession no. X03922, which lacks the 3' terminal 71 base-pairs) is amplified by PCR using the following oligonucleotide primers: "Forward" 5'-TGGCACATGGCCAATGCATT-3' (SEQ ID NO: 3) and "Reverse" 5'-GGCGGAGTTGTTACGA-CATTT-3' (SEQ ID NO: 4). The plasmid pcDNA4 (Invitrogen, Carlsbad, Calif.) can be used as a template for PCR, since it contains the HCMV immediate early promoter. The amplified product does not include the CAT and TATA boxes that are important for transcriptional activity.

Figure 20:
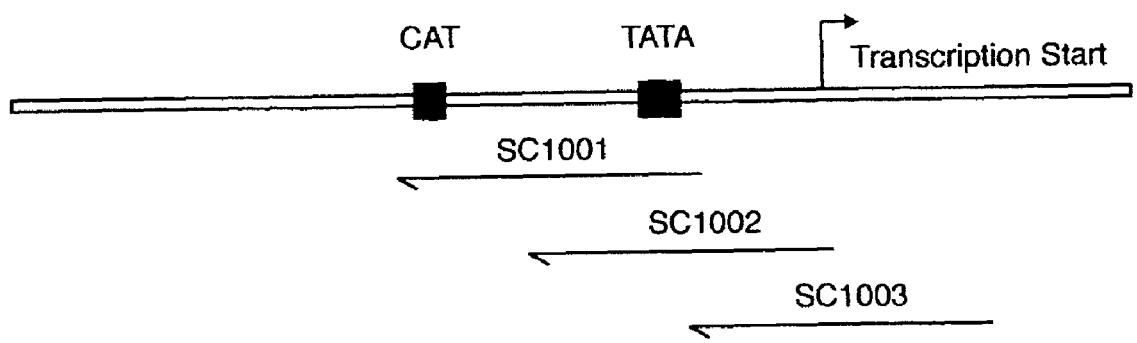
FIG. 20 depicts the positions of three DNA oligonucleotides (each 46-mers; SC1001, SC1002, and SC1003) relative to their complementary regions of the HCMV promoter.

The two PCR products are ligated together using T4 DNA ligase and using standard techniques. The ligation product is then PCR-amplified using routine methods known to those skilled in the art. The ligation product is then cloned into a plasmid vector that does not contain a eukaryotic promoter element, but contains a reporter gene and a polyadenylation signal. An example of such a vector is pGL3 (Promega, Madison Wis.). This vector contains a luciferase reporter gene followed by a polyadenylation signal. Different promoters and promoter enhancer combinations can be cloned into this vector upstream of the reporter gene. These vectors are then transfected into suitable cells and assessed for luciferase expression. Vector A contains the Chimeric HCMV/EF-1α Pmin promoter depicted in FIG. 20. Vector B contains the full-length wild type HCMV promoter. This promoter is generated by PCR using pcDNA 4 as a template and the forward primer already described above. The reverse PCR primer for creating this PCR product maps to the extreme 3' end of the HCMV immediate early promoter. The sequence is: 5'-CG-GTTCACTAAACGAGCTCTG-3' (SEQ ID NO:5). This sequence corresponds to nucleotides 1121-1141 of Genbank accession no. X03922. The above primer is the reverse complement of that sequence. Vector C contains the EF-1α Pmin promoter. Following PCR amplification, the PCR products are cloned into pGL3 using standard techniques.

Analysis of Constructs

Human rhabdomyosarcoma cells (RD) are seeded into six-well plates. When cells are 80-95% confluent, they are transfected with varying amounts of the experimental constructs and Lipofectamine (Gibco-BRL) according to the manufacturer's instructions. Total DNA is held constant at 2.5 ug using pGL3 basic as filler. It is noted that pGL3 basic has no promoter and has been demonstrated not to express detectable levels of luciferase following transfection into RD cells. At 24 and 48 hours post-transfection, cells are lysed and assayed for luciferase activity using the Luciferase Assay system (Promega, Madison, Wis.) according to manufacturer's directions. Luciferase measurements are performed on a luminimeter. An example of a luminometer is the Berthold Microlumat LB 96P. $V_{max}$ and $K_m$ values are derived following expression analysis as described herein.

Desirably, the chimeric HCMV/EF-1α Pmin promoter has a lower $K_m$ than the HCMV promoter and a $V_{max}$ that lies between the $V_{max}$ values of the EF-1α Pmin promoter and the HCMV promoter. Accordingly, one aspect of the invention provides a nucleic acid molecule encoding the chimeric HCMV/EF-1α Pmin promoter. In another aspect, the invention provides a nucleic acid molecule in which the chimeric HCMV/EF-1α Pmin promoter is operably linked to an RNA or protein coding sequence of interest. Also envisioned are methods of expressing an RNA or protein of interest utilizing expression constructs comprising the chimeric HCMV/EF-1α Pmin promoter.

Other chimeric promoters in which the EF-1α Pmin promoter is positioned within other regions of the HCMV promoter are expected to exhibit advantageous characteristics. In addition, other chimeric promoter constructs incorporating the EF-1 α Pmin promoter and other regulatory elements can be readily constructed by those of skill in the art and evaluated utilizing the methods disclosed herein. Other promoters in addition to HCMV that are useful for such manipulations include, but are not limited to, promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (e.g., HCMV, such as the CMV immediate early promoter, as well as MCMV and SCMV), Epstein Barr Virus (EBV), Rous Sarcoma Virus (RSV) as well as promoters from human genes such as human actin, human myosin, human hemoglobin, human muscle creatine, human metalothionein, and human mitochondrial promoter The preparation or synthesis of the nucleotide sequences and cloning techniques described herein are well within the ability of a person having ordinary skill in the art using available material.

Example 3

Forced Open Promoter Complex

The function of a promoter is to affect transcriptional initiation, the rate-limiting step in transcription. The traditional approach to improving promoter functionality has been through the identification and optimization of nucleic acid sequences with desirable properties which result in high level transcription initiation. To date, attempts to create an unregulated promoter have been unsuccessful.

Figure 10:
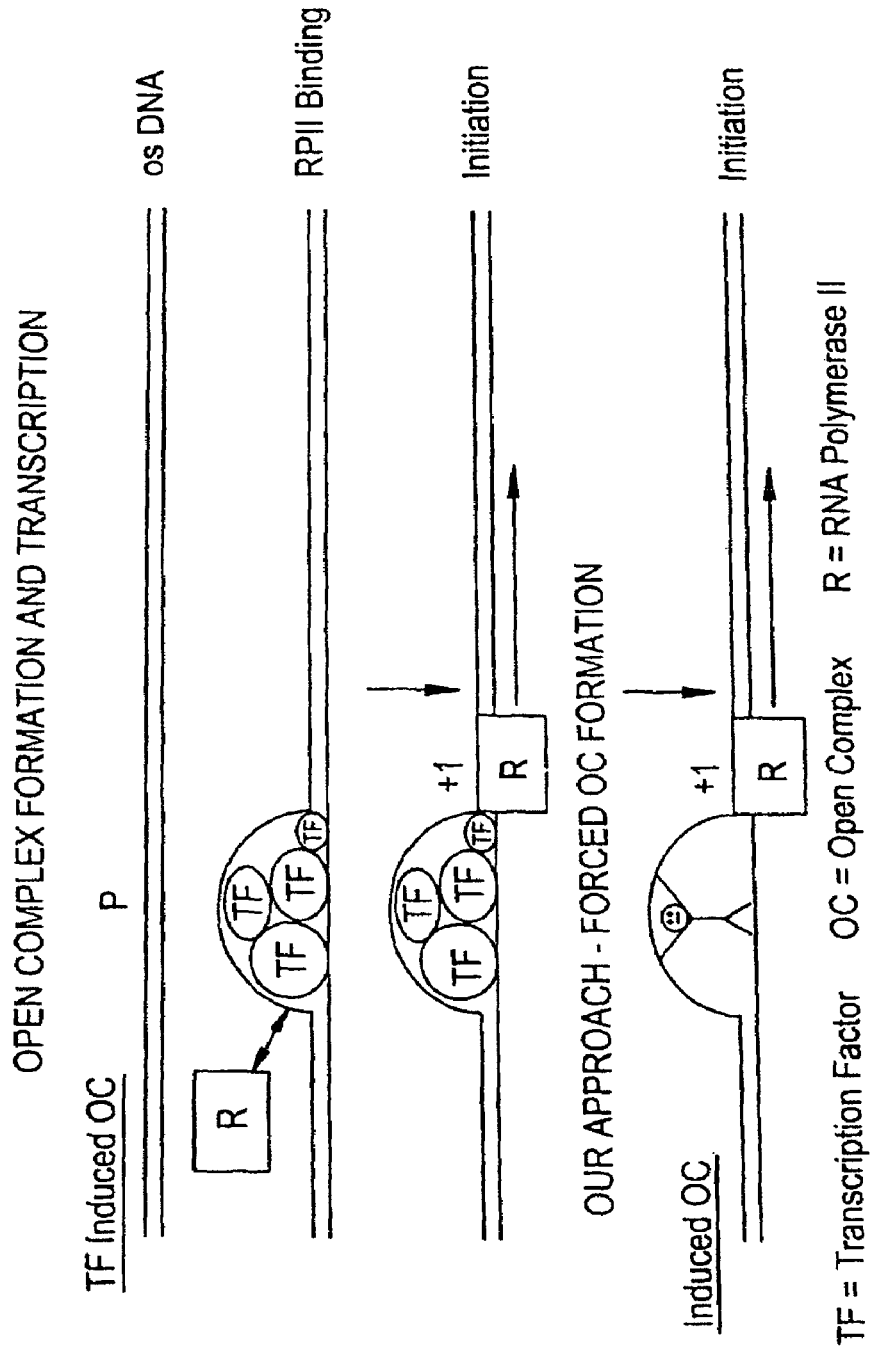
FIG. 10 is a schematic of open complex formation under normal (transcription factor/polymerase-induced) and forced conditions.

The rate of transcription initiation is limited by open complex formation (melting of the transcriptional start site), and is dependent on the promoter sequence and the transcription factors that bind the promoter sequences (FIG. 9). A bubble of unbase-paired DNA resembles the transcription bubble associated with open promoter complexes. Transcription from these bubbles is stimulated in excess of a hundred-fold relative to the completely duplexed promoter elements, suggesting that blocking complete base-pairing within a promoter sequence can generate open promoter complexes (Tantin and Carey, 1994 J. Biol. Chem. 269, 17397-17400 and Pan and Greenblatt, 1994 J. Biol. Chem. 269, 30101-30104). Supercoiled DNA throws out single stranded DNA loops in order to release torsional stress. Loop formation is random and dynamic (FIG. 10) (Bentin and Nielsen 1996 Biochem. 35, 8863-8869). When oligonucleotide concentrations are high relative to plasmid concentrations, the loops anneal to complementary oligonucleotides instead of the partner plasmid strand. This creates a heteroduplex. Furthermore, potassium permanganate probing reveals that the regions of plasmid DNA on either side of the annealed oligonucleotide are not base-paired with the partner plasmid DNA strand. This base-pairing is presumably thermodynamically unfavorable. The heteroduplex between the oligonucleotide and the supercoiled vector, creating a free single strand in the vector, creates an open promoter complex which favors transcriptional initiation.

Figure 18:
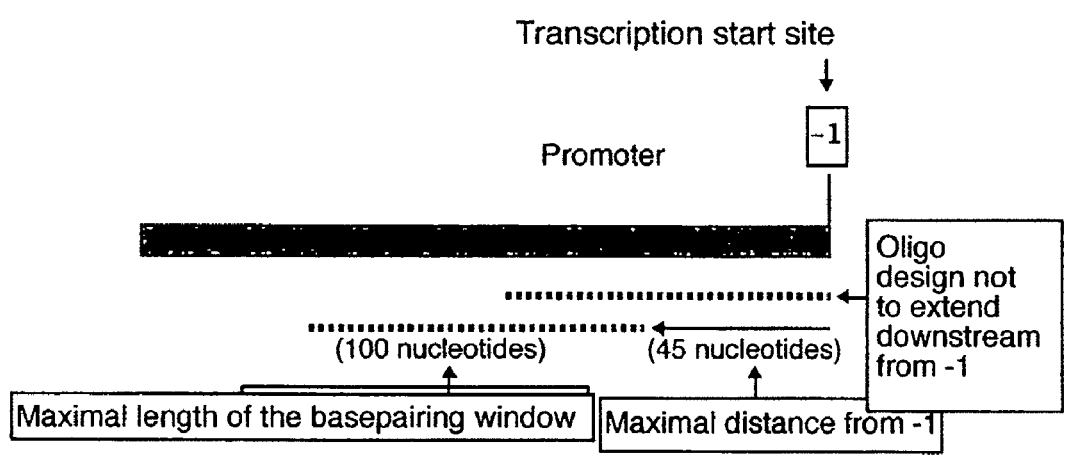
FIG. 18 depicts the desirable features for padlocked and non-padlocked oligonucleotides. The oligo desirably does not base-pair with sequences downstream from the −1 position of the promoter of interest and to preferentially base-pair with sequences located between −1 and −45 of the promoter of interest. The desirable maximal length of the oligo is 100 nucleotides and the desirable minimal length is 12 nucleotides.

An unregulated, or super promoter, is formed if the heteroduplex is stabilized for an indefinite period of time. We have discovered that stabilization is enhanced by creating a heteroduplex "padlock" on the promoter sequence. DNA padlocking is performed by incubating supercoiled plasmids with a relatively high concentration (e.g., 1000 fold molar excess) of a linear DNA (padlock) containing a 5' end that is complementary to a sequence of the target DNA molecule, and a 3' end that is complementary to a contiguous sequence of the target DNA molecule. The linear DNA molecule base-pairs to the target supercoiled plasmid, thereby juxtaposing the 3' and the 5' ends of the linear molecule annealed to adjacent bases on the target sequence. The regions of complementarity of the 5' and 3' ends of the DNA must be contiguous and should each be at least five nucleotides in length. Once in position, the two ends of the linear sequence are ligated to form a circular nucleic acid (e.g., DNA) with at least 10 bases (at least five at each end of the linear sequence that are annealed to the target) that are hydrogen-bonded to the target sequence. This ligation allows the oligo to contain at least one linking number with respect to the target sequence resulting in one helical turn. In various embodiments, the oligonucleotide is a DNA, an RNA, a PNA, or a mixture thereof. In desirable embodiments, the single stranded oligonucleotide comprises at least five contiguous nucleotides at the 5' terminus that are complementary to a first region of the supercoiled DNA or RNA and at least five contiguous nucleotides at the 3' terminus that are complementary to a second region of the supercoiled DNA or RNA that is adjacent to the first region. Desirably, the first and/or second regions of one strand of the supercoiled DNA or RNA that are 100% complementary to the 5' or 3' terminus of the single stranded oligonucleotide are at least 6 to 10 or 10 to 20 nucleotides, more desirably at least 30 nucleotides, most desirably at least 40 nucleotides or even at least 50 nucleotides or 100 nucleotides in length. The first and second regions of complementarity may be the same or different lengths. The schematic diagram in FIG. 18 depicts the design features of forced open complexes prepared using an oligo or a padlock with respect to the transcription start site. The 3' and 5' complementary sequences on the supercoiled DNA or RNA are next to each other so that when the oligonucleotide is annealed to the supercoiled DNA or RNA, the 3' and the 5' terminal nucleotides of the single stranded oligonucleotide base-pair with adjacent bases in the supercoiled DNA or RNA and can be ligated 3' to 5' to form a molecule torsionally locked to the supercoiled DNA or RNA. In one aspect, a phosphodiester linkage is formed between the 3' and the 5' ends of the single stranded oligonucleotide. In addition to the complementary 5' and 3' sequences, the oligonucleotide desirably includes a region linking the 5' and the 3' ends that is at least as long, and desirably longer to avoid torsional stress, than the total length of the complementary 5' and the 3' sequences. In one embodiment, the linking region consists of nucleotides with naturally-occurring or modified bases.

Figure 11:
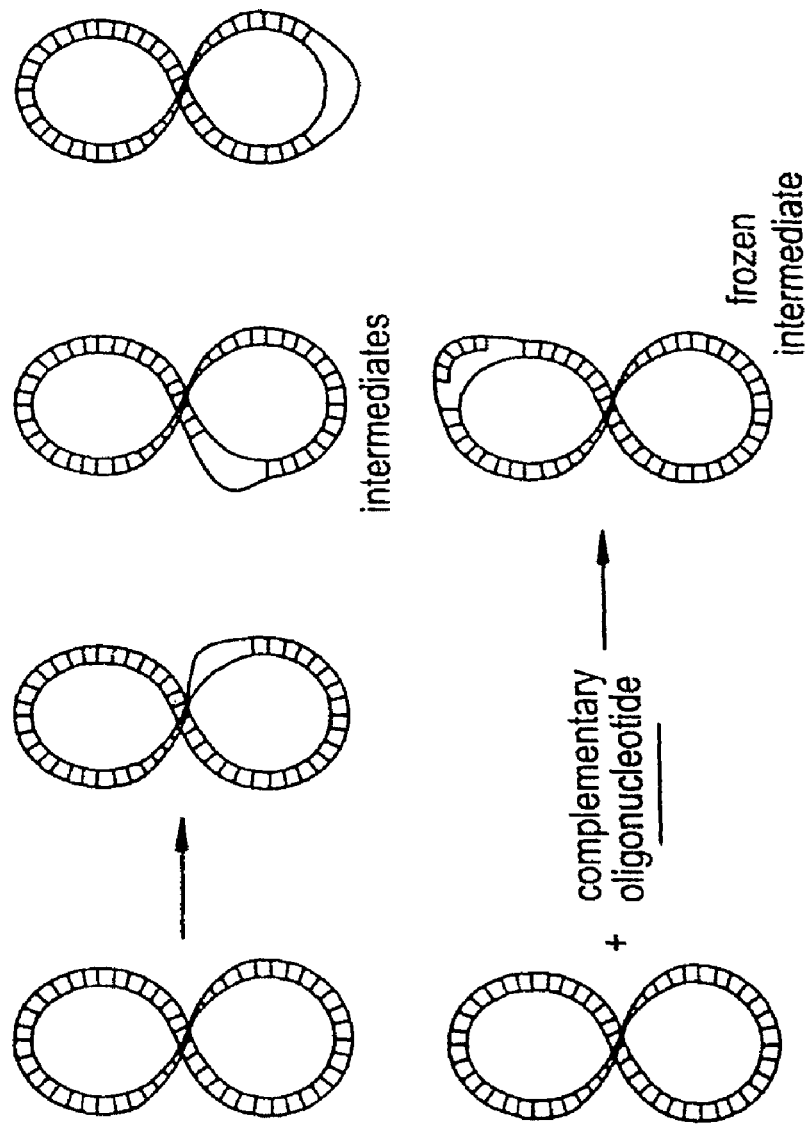
FIG. 11 is a schematic showing the natural "breathing" of supercoiled DNA, and a strategy for creating an open complex by forming a heteroduplex within the supercoil.
Figure 12:
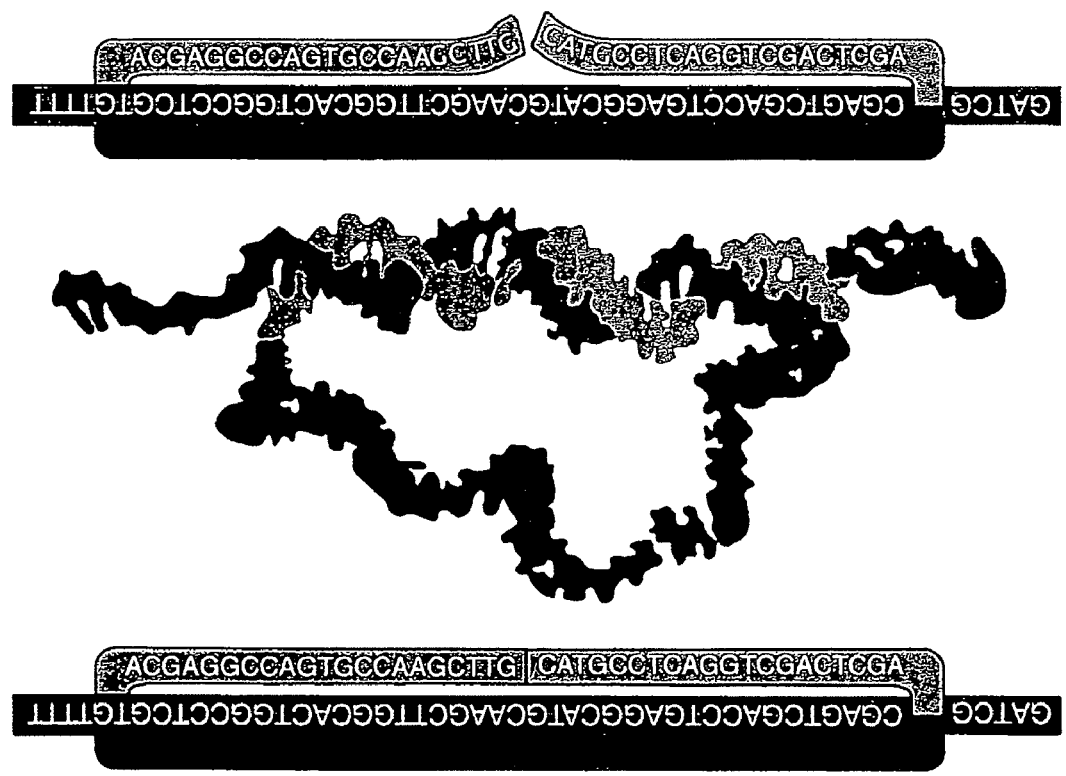
FIG. 12 is a schematic demonstrating the molecular mechanism for topologically locked heteroduplex formation in a DNA supercoil (padlock) (SEQ ID NOS:11-14).
Figure 13:
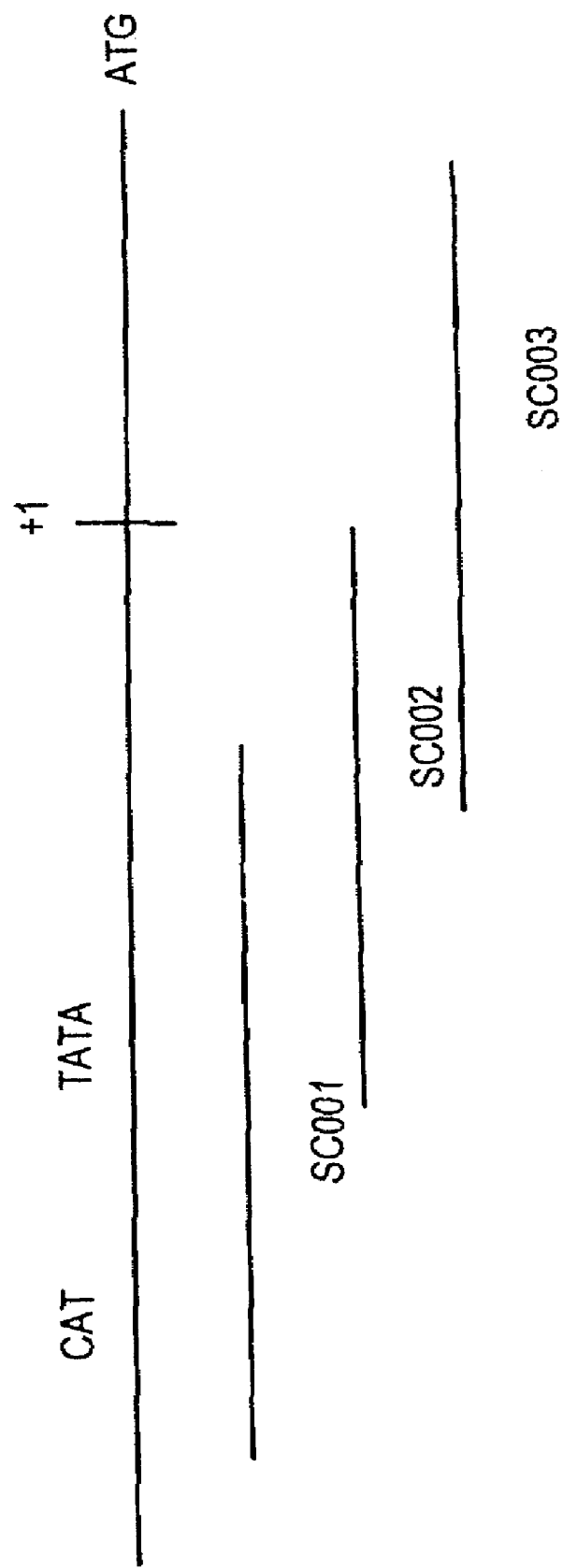
FIG. 13 is a schematic showing the strategy used for designing oligonucleotides useful for heteroduplex formation.
Figure 14A:
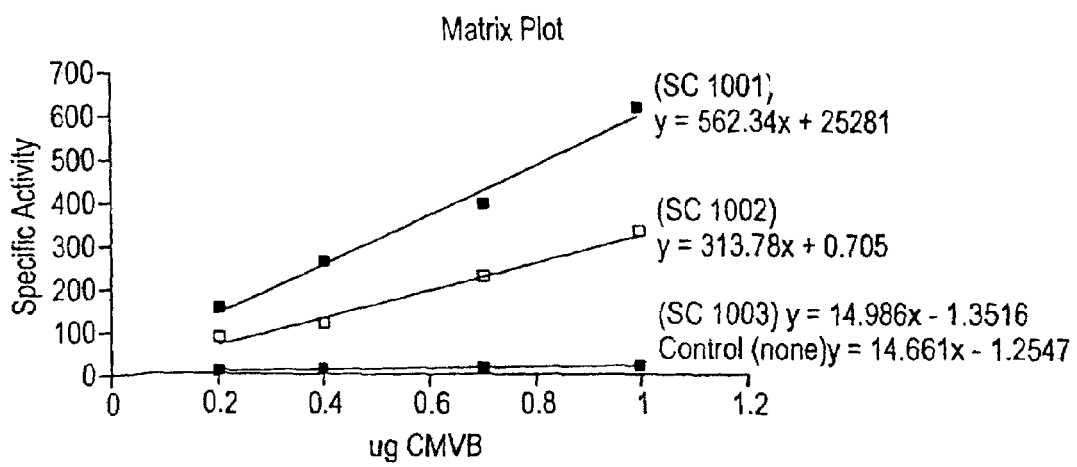
FIGS. 14A and 14B are graphs comparing the β-gal activity in RD cells transfected under sub-saturating conditions in which the vector was incubated with synthetic oligonucleotides of varying lengths, sequences, and specificities. Both the Michalis-Menten and Lineweaver-Burk plots are shown.
Figure 14B:
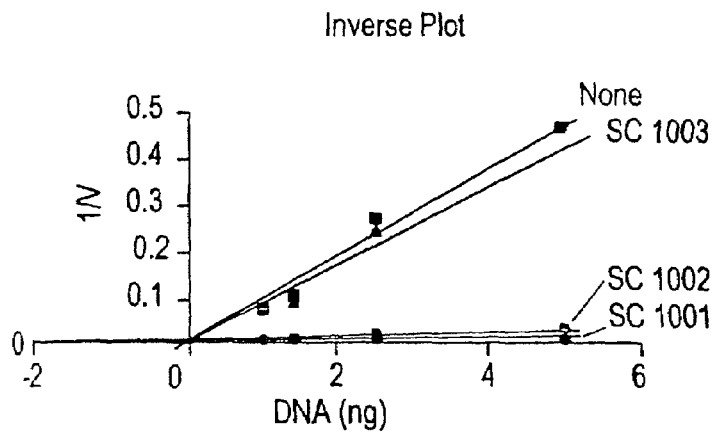

The intervening, connector sequence (linking region) can be a random sequence that is not complementary to any portion of the vector, or can be a sequence useful for targeting a cell type, or a sequence that binds either a polymerase or transcription factor and desirably enhances transcription by bringing this factor or polymerase to proximity with respect to the padlocked sequence. Examples of such useful, non-random sequences include sequences that promote RNA polymerase binding, such as minimal sequences of EF-1 alpha. Subsequent to annealing of the vector DNA and the padlock DNA, the padlock DNA is ligated by chemical or enzymatic means (FIG. 11). Chemical ligation can be carried out using linking technologies such as those using maleimide, carbodiimide, or succinamide technologies (Pierce), or the hydrazine-aldehyde linkages described by Solulink (www-.solulink.com, San Diego, Calif.). For example, an oligonucleotide with an aldehyde can be ligated to an oligonucleotide with a hydrazine on a DNA template, provided the two oligonucleotides are in proximity due to base-pairing to the template such that the end bases of the oligonucleotides become adjacent. Chemical linkage may also be accomplished as described in Luebke and Dervan, J. Am. Chem. Soc., 1989, 111: 8733-8735 and Luebke and Dervan, JACS, 1991, 113. Exemplary template-directed chemical ligation methods are described by Herrlein and Letsinger, Nucleic Acids Res. 1994 Nov. 25:22(23):5076-8; Gryaznov and Letsinger, Nucleic Acids Res. 1993 Mar. 25; 21(6):1403-8; Calderone et al., Angew. Chem. Int. Ed. 2002, 41, No. 21, page 4104; Gartner et al., J. Am. Chem. Soc. (JACS) 2002, 124, 10304-10306; Gartner et al., Angew. Chem. Int. Ed. 2002, 41, No. 10, page 1796; Gartner and Liu, J. Am. Chem. Soc. 2001, 123, 6961-6963. Ligation of the 5' and 3' ends of the padlock DNA forms a knotted structure, where the padlock DNA is wrapped around the vector DNA once for about every ten nucleotides. The resulting heteroduplex is, therefore, stabilized indefinitely, forming a permanent forced-open complex and should be unaffected by transcriptional repressors, or a lack of transcriptional enhancers.

Figure 19:
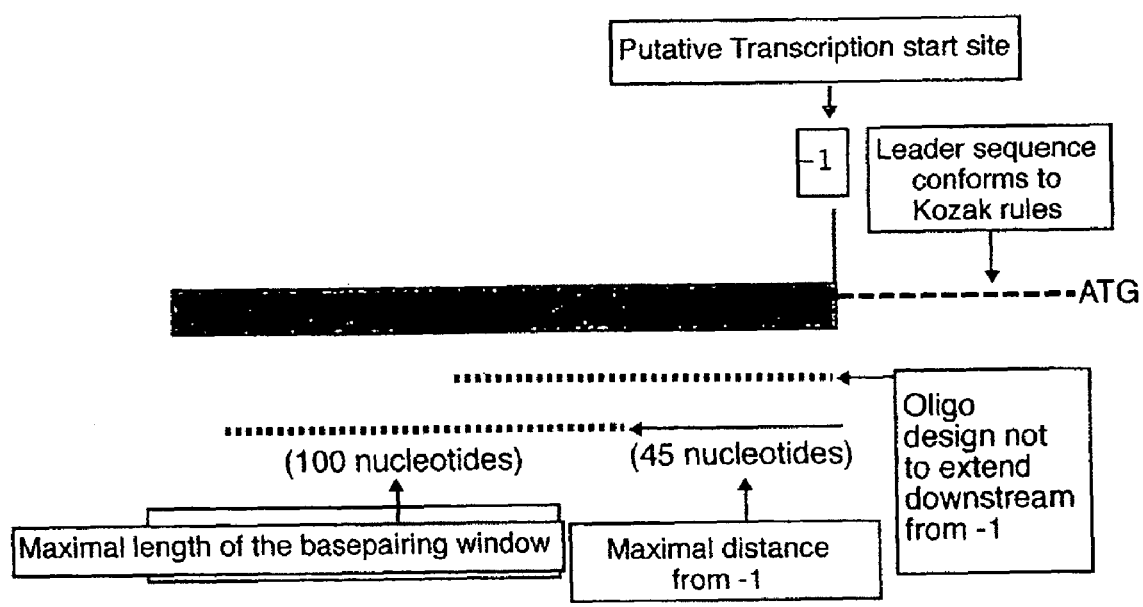
FIG. 19 depicts the method for designing padlocked and non-padlocked oligonucleotides in situations in which there is not a promoter or the location of the promoter is unknown. For transcription of protein-encoding RNAs, oligonucleotides are designed to base-pair at least 20 nucleotides upstream from an initiation codon, more desirably 21-50 nucleotides upstream from the initiation codon, and most desirably 51-80 nucleotides upstream from the initiation codon. For transcription of RNA sequences that are not translated, oligonucleotides are desirably designed to anneal to sequences located about 1-45 nucleotides upstream of the RNA sequences to be transcribed. Desirably, the maximal length of the oligo is 100 nucleotides, and the desirable minimal length is 12 nucleotides.

According to this invention, this technique is not limited to use of previously identified promoter sequences. A permanent forced-open complex can be formed at any DNA sequence and acts to promote transcription of the downstream sequence. The schematic diagram in FIG. 19 depicts the design features of forced open complexes prepared using an oligo or a padlock with respect to the translation initiation site.

Example 4

Forced Open Promoter Complexes

Four oligonucleotides (46-mers) are synthesized. SC1001, SC1002, and SC1003 are each DNAs complementary to a region of the HCMV promoter (FIG. 20), whereas SC1004 is a scrambled oligo. SC1001 is a 46-mer that overlaps the CAT and TATA boxes of the HCMV promoter as contained in the plasmid pCMV-beta (BD Biosciences, Palo Alto, Calif.; GenBank accession #: U02451). SC1002 is a 46-mer that extends to the −1 site of the HCMV promoter. SC1003 is a 46-mer that straddles the +1 site of the HCMV promoter. SC1004 is a scrambled 46-mer with the same nucleotide composition as SC1001, but without complementarity to any region of pCMV-beta. Each of the oligonucleotides is incubated with pCMV-beta vector DNA at a 1000-fold molar excess under standard conditions designed to favor annealing. Various amounts of pCMV-beta complexed with oligonucleotides, including 0.2, 0.4, 0.6, 0.8 or 1 ng of the vector, are used to titrate the range of expression. Each of the annealed oligonucleotide-vector complexes is transfected into $8.5 \times 10^5$ Rhabdomyosarcoma (RD) cells using Lipofectamine (Invitrogen, Carlsbad, Calif.) according to the manufacturer's instructions. As controls, cells are transfected with various amounts of pCMV-beta alone, including 0.2, 0.4, 0.6, 0.8 or 1 ng of the vector per well. The total amount of DNA in all the transfections is adjusted to 2.5 ug with pGL3 (Promega, Madison, Wis.), which acts as filler DNA. At 48 hours post-transfection, the cells are lysed with 500 ul of lysis buffer (300 mM NaCl; 50 mM Tris, pH 7.6; 0.5% Triton X-100; and 0.5% Sodium deoxycholate) for one hour at 4° C. with rocking. Promoter activity is monitored by assaying for β-galactosidase activity according to the protocol described in Sambrook et al. (1989), modified as described in Examples 5A-5C below. $K_m$ and $V_{max}$ values are calculated by procedures described herein.

Desirably, the complementary oligonucleotides yield annealed promoter complexes which function as strong promoters with very low $K_m$ values. Desirably, increases of 50 to 500 fold in $V_{max}$ are observed, depending upon the oligonucleotide selected. The forced open promoter complexes desirably have $K_m$ values at least several hundred fold lower than the native HCMV promoter, indicating that these oligo-annealed promoter constructs may be active at only a few copies or even a single copy per cell. The SC1001-HCMV construct is expected to show maximum enhancement of the reporter expression compared to the corresponding values from cells transfected with uncomplexed reporter plasmid, pCMV-beta. The SC1004 oligonucleotide (which is not complementary to any region of pCMV-beta and does not hybridize to it) is expected to show negligible enhancement over the reporter plasmid alone. The following exemplary sequences may be used:

SC1001 (inverse complement of nucleotides 484-529 of pCMV-beta;
(SEQ ID NO: 6)
5'-tgcttatatagacctcccaccgtacacgcctaccgcccatttgcg
t-3', SC1002 (inverse complement of nucleotides 503-548 of pCMV-beta;
(SEQ ID NO: 7)
5'-cggttcactaaacgagctctgcttatatagacctcccaccgtaca
c-3', SC1003 (inverse complement of nucleotides 526-571 of pCMV-beta;
(SEQ ID NO: 8)
5'-gatggcgtctccaggcgatctgacggttcactaaacgagctctgc
t-3',
and SC1004 (scrambled version of SC1001;
(SEQ ID NO: 9)
5'-gatgatcggatcgagtcggagatcgatggatcggatcggatcgagtc
gagtcag-3.

Example 5A

Generation of Padlocked Supercoiled DNA

The HCMV-β-gal supercoiled plasmid (construct 017) and the pShooter plasmid (Invitrogen) were heated to 95° C. to produce a mixed solution of linear, nicked, and supercoiled plasmid DNA. Plasmid DNA was incubated with linear padlock DNA ($^{32}$P-labeled), with the 5' and 3' ends being complementary to a continuous 38 nucleotide sequence covering the CAT and TATA box of the HCMV promoter. After annealing, the padlock DNA was ligated using a thermostable ligase (Epicenter Inc., Wisconsin, USA) and separated on an agarose gel. FIG. 15 is a photograph of the agarose gel stained with ethidium bromide, showing the presence of all three forms of DNA (supercoiled, nicked, and linear). Also included is an autoradiogram of the same gel showing that only supercoiled DNA is capable of being padlocked. Additionally, the padlock did not bind to the control plasmid.

Example 5B

Forcing Open Known Promoter Sequences with Padlocks

The single stranded oligonucleotide sequence or the torsionally locked padlock oligonucleotide is designed to be complementary to the sequences of the promoter. The ideal method to enhance promoter expression is to design the base-pairing to extend into the promoter region, desirably beginning at sequences −1 to the transcription initiation site on the non-coding strand (i.e, the non-template or non-transcribed strand) of DNA. Alternatively, the oligonucleotide may be designed such that the base-pairing may begin further into the promoter, e.g., at the −45, at the −20, or at the −10 sequence position. Base-pairing to the coding strand (i.e., the transcribed strand) is less desirable. The base-pairing window (i.e., length of complementary sequence) should minimally be 10-12 nucleotides, more desirably 20 to 30, and most desirably 45 nucleotides, but can be up to 100 nucleotides in length. Many RNA polII promoters contain either or both the TATA box at about −25 and the CAT box at or near the −45 sequence region preceding the transcription initiation site. Base-pairing to one or desirably both elements (e.g., the TATA and CAT box) may be used in some embodiments. Desirably, the oligonucleotide base-pairs to the element nearest to the −1 position.

While a complementary torsionally locked padlock oligonucleotide, DNA, RNA, or PNA provides a stable, forced open promoter that is particularly advantageous for certain applications, it is recognized that non-padlocked linear or circular single stranded olignucleotide sequences, (e.g., DNA, RNA, PNA, or hybrids thereof) may also be annealed as described to promoter sequences to provide forced open promoters with enhanced, though less stable, activity. Single stranded or circular non-padlocked oligonucleotides, (e.g., DNA, RNA, PNA, or hybrids thereof) are annealed as described herein to one strand of a double stranded DNA or RNA (desirably to a promoter sequence or another sequence upstream from and operably linked to an RNA or protein coding sequence of interest) but not torsionally locked between the two DNA or RNA strands as with a padlock oligonucleotide. Furthermore, while such forced open promoters are advantageously prepared using promoters found in supercoiled DNA or RNA expression constructs or vectors, these methods and constructs are also applicable to forced open promoters within nicked, covalently closed circular, or linear DNA or RNA expression constructs, as well as other non-promoter sequences within such supercoiled, nicked, closed circular, or linear expression constructs capable of expressing mRNA and optionally also protein. While it is desirable to make the various forced open promoter constructs on supercoiled DNA or RNA, if the construct is subsequently nicked, linearized, or converted to a covalently closed circular DNA or RNA, it will still function as described herein, albeit with potentially altered efficiency.

Example 5C

Generation of a Padlocked HCMV Promoter

Five ng pCMV-beta plasmid (BD Biosciences, Palo Alto, Calif.; GenBank accession #:U02451) is incubated with 1000-fold molar excess of padlock oligonucleotide #1 (described below) under conditions favoring annealing of padlock oligo to pCMV-beta. The sequence of the padlock oligo is designed to anneal to the HCMV promoter in the plasmid. Incubation is carried out in a volume of 15 ul of AmpLigase buffer and 5 u Ampligase Thermostable DNA ligase (Epicentre, Madison, Wis.) in a thermocycler. Incubation temperature is initially set at 65° C. The temperature is ramped down by 2° C. every 10 minutes until a final temperature of 50° C. is reached, at which point the reaction is terminated. During the reaction, the 3' and the 5' ends of the oligo are annealed to contiguous sequences of pCMV-beta. Then, ligation of the abutting 3' and 5' ends of the annealed oligo occurs, generating the padlocked oligo structure shown in FIG. 16. As shown, padlock oligonucleotide #1 is annealed to pCMV-beta. The 5' twenty-eight nucleotides base-pair with nucleotides mapping to coordinates −47 to −20 of the HCMV promoter present in pCMV-beta. The internal nucleotides do not base-pair with pCMV-beta. They are included to (i) give the oligonucleotide freedom to rotate its termini to facilitate base-pairing and (ii) prevent additional torsional stress to the supercoiled pCMV-beta following annealing of the padlock oligo. Once annealed, the oligo is ligated to create a phosphodiester linkage between the 3' and the 5' termini of the oligo generating the padlocked oligo structure. Regions flanking the annealed padlock oligo are single-stranded due to torsional constraints.

One advantage of using padlocked oligonucleotides relative to annealed single-stranded non-padlocked oligonucleotides is that padlocked oligonucleotides are stably annealed to the DNA and are only released following nicking of the oligo or the region of DNA to which the oligo is annealed. This factor makes plasmids containing padlocked oligonucleotides ideal for in vivo use, although they can be used for in vitro applications as well. For certain applications, linear oligonucleotides annealed to promoter sequences in supercoiled DNA or RNA plasmids can advantageously be employed to achieve enhanced expression similar to that described below, although less sustained for in vivo applications. In some applications this more transient effect is advantageous.

Figure 16:
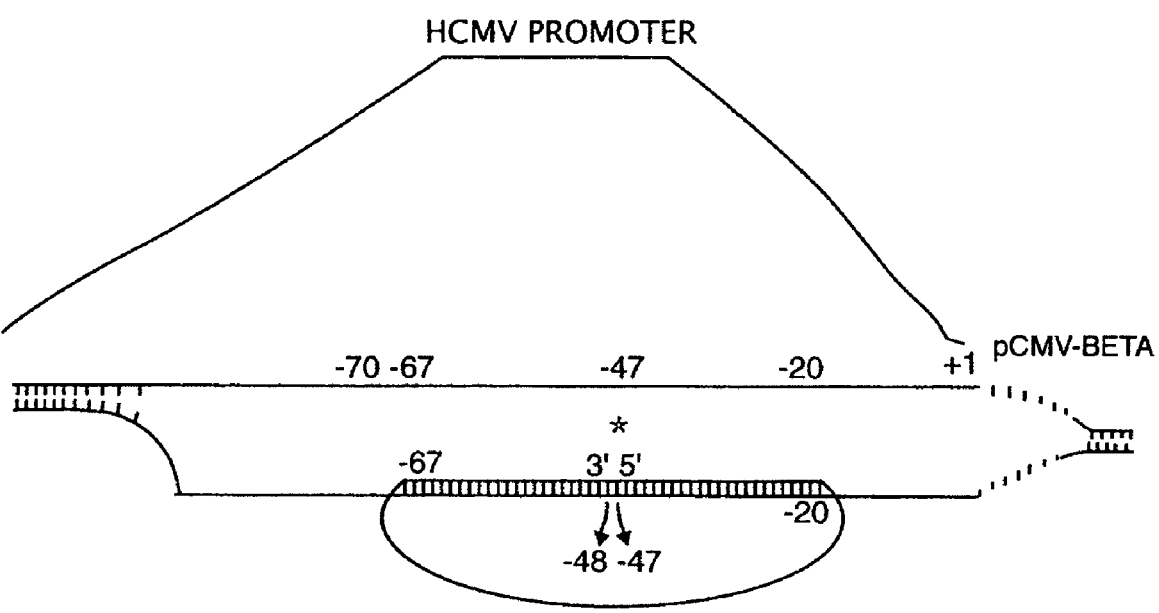
FIG. 16 depicts padlock oligonucleotide #1 being annealed to pCMV-beta as described herein. The 5' twenty-eight nucleotides of the padlock oligonucleotide base-pair with nucleotides mapping to coordinates −47 to −20 of the HCMV promoter present in pCMV-beta, and the 3' twenty nucleotides base-pair to nucleotides mapping to coordinates −48 to −67. Therefore, the 3' and the 5' ends are base-paired to adjacent nucleotides ("*," nucleotides −47 and −48) of the HCMV Promoter in pCMV-beta and are positioned for ligation. The internal nucleotides linking the 3' and 5' sequences do not base-pair with pCMV-beta. These nucleotides (i) give the oligonucleotide freedom to rotate its termini to facilitate base-pairing and (ii) prevent additional torsional stress to the supercoiled pCMV-beta following annealing of the padlock oligo. Once annealed, the oligo is ligated to create a phosphodiester linkage between the 3' and the 5' ends of the oligo (*) generating the padlocked oligo structure. Regions flanking the annealed padlock oligo are single-stranded due to torsional constraints.

The Padlock oligo #1 sequence is presented below: 5' GTGTACGGTGGGAGGTCTATATAAGCAGTCGAGTT AATTAACGGCCGTC TAGAGGTACCGAAT- TCGCTAGCGCGGCCGCCGATCGGTCGACG GACGCAAATGGGCGGTAGGC3' (SEQ ID NO: 10). Underlined sequences represent those oligo sequences that bind to sequences in the HCMV promoter as depicted in FIG. 16. The 5' underlined sequences (5'-3' direction) map to coordinates 503-530 of GenBank accession number U02451, and the 3' underlined sequences (5'-3' direction) map to coordinates 483-502 of GenBank accession number U02451. These sequences represent coordinates −47 to −20 and −67 to −48 of the HCMV promoter, respectively.

Transfection

The annealing and ligation reaction mix is sufficient for five transfections. Transfection mixtures are comprised of 3 ul annealing/ligation mixture (corresponding to about 1 ng padlocked promoter plasmid) and 2.5 ug pGL3 basic (Promega, Madison, Wis.) as filler DNA in a volume of 10 ul. Approximately $8.5 \times 10^5$ RD cells are transfected using Lipofectamine™ (Invitrogen, Carlsbad, Calif.) according to the manufacturer's directions. Control cells are transfected with transfection mixtures containing 1 ng, 5 ng, 50 ng, or 100 ng unpadlocked pCMV-beta. These transfection mixtures contain pGL3 basic DNA as filler DNA such that the total amount of DNA per transfection is 2.5 ug. At 48 hrs post-transfection, the cells are lysed with 500 ul lysis buffer (300 mM NaCl: 50 mM Tris, pH 7.6, 0.5% Triton X-100, and 0.5% NaDeoxycholate) for one hour at 4° C., with rocking. Promoter activity is monitored by assaying for B-galactosidase using a modification of the protocol described in *Molecular Cloning, A Laboratory Manual*, 2nd Edition, Sambrook et al., Cold Spring Harbor Press, Plainview, N.Y. (1989). The modification is that readings are taken every minute for 90 minutes following setting up the B-Gal enzyme assay. Readings are taken on a kinetic plate reader such as the VersMax Tunable Microplate reader (Molecular Devices, Sunnyvale, Calif.). $V_{max}$ values are calculated by procedures determined herein. Desirably, the padlocked pCMV-beta plasmids generate higher $V_{max}$ values following transfection relative to the unpadlocked pCMV-beta plasmids. In desirable embodiments, values are typically 50-500 fold higher, which would indicate that 50-500 fold less plasmid can be administered (relative to unpadlocked plasmid) without a loss in expression.

Example 5D

Generation of Padlocked Promoter

The expression vector used for these experiments is pCMV-SEAP, a proprietary eukaryotic SEAP (placental heat-stable SEcreted Alkaline Phosphatase) expression vector. This vector contains the SEAP expression cassette from pSEAP2-Control plasmid (Clontech, Palo Alto, Calif.; GenBank Accession# U89938) and includes the SEAP coding region and the 5'UTR (coordinates 249-1831 of pSEAP2-Control). This region was cloned into a plasmid vector under the transcriptional control of the HCMV promoter described herein. A BGH polyadenlyation site provides the polyadenylation signal. Cloning is performed using standard techniques. Approximately 100 ng pCMV-SEAP is incubated with 1000-fold molar excess of padlock oligonucleotide #1 described above under conditions favoring annealing of padlock oligo to pCMV-SEAP. The reaction is split into three reaction tubes of 100 ul each. The reaction mixture includes 1× Ampligase buffer, and each 100 ul reaction contains 35 u of Ampligase (Epicentre, Madison, Wis.). The padlock oligo is designed to anneal to the HCMV promoter. The incubation is carried in a thermocycler and the incubation temperature is initially set at 65° C. The temperature is ramped down by 2° C. every 10 minutes until a final temperature of 50° C. is reached at which point the reaction is terminated. During the reaction, annealing of the oligo to pCMV-SEAP occurs. Then, ligation of the 5' and 3' ends of the annealed oligo occurs, generating a padlocked oligo structure. One advantage of using padlocked oligonucleotides relative to annealed linear oligonucleotides is that padlocked oligonucleotides are stably annealed to the DNA and are only released following nicking of the oligo or the region of DNA to which the oligo is annealed.

To test the in vivo effects of a padlock, the padlocked pCMV-SEAP plasmid constructs and unpadlocked pCMV-SEAP plasmids are prepared in 30 mM citrate buffer (0.15M NaCl 0.1% EDTA and 0.25% bupivicaine), pH 6.5 to 6.8, at a concentration of 0.1 mg/ml of the padlocked pCMV-SEAP plasmid. Inert filler DNA, pGL3 basic, described herein, is included to bring total DNA concentration to 2 mg/ml. The unpadlocked DNA construct is prepared similarly except that in addition to being formulated at 0.1 mg/ml, additional formulations of 0.50 mg/ml, 1 mg/ml and 2 mg/ml are prepared. Final DNA concentrations are all adjusted to 2 mg/ml with pGL3 basic. A 100 ul dose of each formulation is injected intramuscularly into the quadriceps of mice. There are five mice per each formulation group. At five days postinjection when in vivo plasmid expression peaks, blood is taken from the injected mice by retro-orbital bleed, and the level of SEAP in the sera is determined using the assay described below.

SEAP activity is determined in a kinetic SEAP enzyme assay. According to the SEAP assay, 5-10 ul heat-inactivated sera is added to each well in a 96-well plate. Substrate solution (200 ul) prepared by dissolving 1 vial ALP 20 (alkaline phosphatase, Sigma 245-20) in 20 mL water at room temperature is added to each well. Each well is read immediately using an OPTI max tunable microplate reader (Molecular Devices Co., Sunnyvale, Calif.) at 405 nm kinetic mode, and additional readings are taken every minute for 60 minutes. The linear window of the plot is used for analysis. The slopes of the linear plot are used to compare the relative in vivo expression levels.

Mice injected with the formulation containing the padlocked pCMV-SEAP plasmid desirably express SEAP at levels exceeding those levels occurring in mice injected with any of the formulations containing the non-padlocked pCMV-SEAP, which would indicate that expression from an expression vector can be increased in vivo through the use of padlock oligo invasion of the promoter used to drive expression of the gene of interest. Other animal models may be used similarly.

Generating Open Promoter Complexes De Novo

The design of the complementary linear or padlock oligonucleotide is similar to the one described above, with base-pairing to occur desirably on the non-coding strand. However, since there is no promoter per se, the −1 position is arbitrarily assigned. The −1 position is selected such that the base-pairing window is at least 45 nucleotides (e.g., between 80 and 150 nucleotides) prior to the initiating ATG codon. The sequences between the arbitrary −1 site and the downstream ATG codon desirably conform to all or most of the Kozak rules (e.g., no ATGs, few or no major secondary structures (DeltaG<40 Kcal)). The design features that relate to positioning the oligo or the padlock to achieve transcription and/or translation are shown in FIG. 19.

The complementary single stranded oligonucleotides and the padlock oligonucleotides described herein may be DNA, RNA, PNA (peptide nucleic acid), or a hybrid thereof (Gambari, Curr Pharm Des 2001 November; 7(17):1839-62). They may also contain backbone modifications. For example, internucleotide linkages other than phosphodiester bonds, such as phosphorothioate, methylphosphonate, methylphosphodiester, phosphorodithioate, phosphoramidate, phosphotriester, or phosphate ester linkages (Uhlman et al., Chem. Rev. 90(4):544-584, 1990; Anticancer Research 10: 1169, 1990) may be present in the oligonucleotides to increase their stability. Oligonucleotide stability may also be increased by incorporating 3'-deoxythymidine or 2'-substituted nucleotides (e.g., alkyl substitutions) into the oligonucleotides during synthesis by providing the oligonucleotides as phenylisourea derivatives or by having other molecules, such as aminoacridine or poly-lysine, linked to the 3' ends of the oligonucleotides (see, e.g., Anticancer Research 10:1169-1182, 1990). Modifications of the RNA and/or DNA nucleotides comprising the oligonucleotides of the invention may be present throughout the oligonucleotide, or in selected regions of the oligonucleotide (e.g., the 5' and/or 3' termini). The oligonucleotides may also be modified in their non-base-pairing regions to increase their ability to penetrate a target tissue. For example, the oligonucleotide may be covalently coupled to lipophilic compounds, receptor ligands, or moieties known to enhance endosomal escape. The oligonucleotides of the invention can be made by any method known in the art, including standard chemical synthesis, ligation of constituent oligonucleotides, and transcription of DNA encoding the oligonucleotides.

The non-base-pairing regions of the single stranded oligonucleotide or padlock molecule may be modified to contain covalently linked delivery agents and/or single stranded and double stranded DNA sequences that specifically bind transcription factors and polymerases. These regions may also contain secondary structure and include known binding sites for transcriptional factors, e.g., RNA polII, as well as other polymerases such as RNA polIII, mitochondrial RNA polymerase, T7, and vaccinia. While single-stranded, non-padlock oligonucleotides of the invention are frequently linear molecules, it is contemplated that circular oligonucleotides may also be utilized advantageously. Such circular single stranded oligonucleotides may include a region of at least 10-12 nucleotides complementary to a target region of a supercoiled DNA or RNA and the non-base-pairing linker region may advantageously include any of the modifications described above (e.g., nucleotides with binding sites, receptor ligands to target cells, or agents to promote delivery or endosomal escape).

The non-base-pairing region may include, for example, nucleotides, PEGs, peptides, and/or proteins. Examples of such delivery agents and other covalent linkages include compositions containing optional polynucleotide facilitating agents or "co-agents," such as a local anaesthetic, a peptide, a lipid (e.g., a cationic lipid), a liposome or lipidic particle, a polycation such as polylysine, a branched, three dimensional polycation such as a dendrimer, a carbohydrate, a cationic amphiphile, a detergent, a benzyl ammonium surfactant, or another compound that facilitates polynucleotide transfer to cells. Non-exclusive examples of such facilitating agents or co-agents useful in this invention are described in U.S. Pat. Nos. 5,593,972; 5,703,055; 5,739,118; 5,837,533; International Patent Application No. WO96/10038, published Apr. 4, 1996; and International Patent Application No WO94/16737, published Aug. 8, 1994, which are each incorporated herein by reference. The linkage can be produced using phosphoramidite chemistry methods to link non-nucleosides to the oligonucleotide or padlock or using standard chemistry methods to modify a nucleotide or base in the oligonucleotide or padlock. Desirable padlocks and oligonucleotides base-pair with the non-template strand of the DNA. Alternatively, padlocks or oligonucleotides that base-pair to the template strand may be used.

Examples of promoters useful for creating open promoter complexes according to the present invention include, but are not limited to, promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (HCMV, such as the CMV immediate early promoter, as well as MCMV and SCMV), Epstein Barr Virus (EBV), Rous Sarcoma Virus (RSV) as well as promoters from human genes such as human actin, human myosin, human hemoglobin, human muscle creatine, human metalothionein, and human mitochondrial promoter.

Other Embodiments

It will be readily recognized to those of skill in the art of molecular biology, biotechnology, and recombinant DNA technology that the forced open promoters and promoter constructs of the invention may be useful in any application utilizing transcriptional promoters, including without limitation production of RNA or protein molecules in cell culture and in vivo applications such as gene therapy, DNA immunization, and gene silencing (e.g. antisense, PTGS, and RNAi). Exemplary PTGS and RNAi applications are described in U.S. provisional application Ser. No. 60/419,532, filed Oct. 18, 2002 and European publication number 1229134, filed Jan. 31, 2002.

From the foregoing description, it will be apparent that variations and modifications may be made to the invention described herein to adopt it to various usages and conditions. Such embodiments are also within the scope of the following claims.

All publications, patents, and patent applications mentioned in this specification are herein incorporated by reference to the same extent as if each individual publication, patent, or patent application was specifically and individually indicated to be incorporated by reference.

What is claimed is:

1. A composition comprising a supercoiled DNA comprising a promoter sequence annealed to a torsionally locked DNA oligonucleotide, wherein said promoter sequence is operably linked to a nucleic acid sequence.

2. A method for generating an open-promoter complex comprising:
   (i) providing a purified plasmid in supercoiled form, the plasmid containing a sequence for expression;
   (ii) creating a padlocked DNA oligonucleotide to generate an open-promoter complex for said sequence for expression.

3. A composition, comprising:
   a purified plasmid DNA in supercoiled form, the construct containing a sequence for expression; and
   a padlocked DNA oligonucleotide annealed to said construct, wherein the padlocked DNA oligonucleotide generates an open-promoter complex for said sequence for expression.

4. The composition of claim 1, wherein the promoter sequence is an HCMV promoter sequence.

5. The composition of claim 1, wherein the nucleic acid sequence encodes an RNA or a protein.

6. The composition of claim 1, wherein the DNA oligonucleotide is annealed to the non-coding strand of the supercoiled DNA.

7. The composition of claim 1, wherein the DNA oligonucleotide is base-paired with the promoter sequence beginning at sequences −1 to the transcription initiation site of the nucleic acid sequence.

8. The composition of claim 1, wherein the DNA oligonucleotide is base-paired with the promoter sequence within a region of about −10 to about −70 from the transcription initiation site of the nucleic acid sequence.

9. The method of claim 2, wherein the sequence for expression is operably linked to a promoter.

10. The method of claim 9, wherein the padlocked DNA oligonucleotide is annealed to a TATA or CAT box within the promoter.

11. The method of claim 9, wherein the padlocked DNA oligonucleotide is annealed to the non-coding strand of the supercoiled DNA.

12. The method of claim 9, wherein the padlocked DNA oligonucleotide is annealed to the coding strand of the supercoiled DNA.

13. The method of claim 2, wherein the sequence for expression is not operably linked to a promoter.

14. The method of claim 13, wherein the sequence for expression contains an initiating ATG codon or is a dsRNA coding region.

15. The method of claim 14, wherein the padlocked DNA oligonucleotide is annealed to the non-coding strand of the supercoiled DNA.

16. The method of claim 14, wherein the padlocked DNA oligonucleotide is annealed to the coding strand of the supercoiled DNA.

17. The composition of claim 3, wherein the sequence for expression is operably linked to a promoter.

18. The composition of claim 17, wherein the padlocked DNA oligonucleotide is annealed to a TATA or CAT box within the promoter.

19. The composition of claim 17, wherein the padlocked DNA oligonucleotide is annealed to the coding strand of the supercoiled DNA.

20. The composition of claim 17, wherein the padlocked DNA oligonucleotide is annealed to the coding strand of the supercoiled DNA.

21. The composition of claim 3 wherein the sequence for expression is not operably linked to a promoter.

22. The composition of claim 21, wherein the sequence for expression contains an initiating ATG codon or is a dsRNA coding region.

23. The composition of claim 22, wherein the padlocked DNA oligonucleotide is annealed to the non-coding strand of the supercoiled DNA.

24. The composition of claim 22, wherein the padlocked DNA oligonucleotide is annealed to the coding strand of the supercoiled DNA.

25. A method for producing a forced open promoter complex, wherein the forced open promoter complex promotes an increase in transcription of a nucleic acid sequence, the method comprising:
   annealing a single stranded RNA oligonucleotide of 12 to 100 nucleotides to a supercoiled DNA comprising the nucleic acid sequence, wherein the RNA oligonucleotide anneals to the supercoiled DNA at a target sequence between nucleotides −1 and −45 of the promoter of the nucleic acid sequence and wherein the 5' end of the RNA oligonucleotide anneals to an upstream end of the target sequence, wherein the 3' end of the RNA oligonucleotide anneals to a downstream end of the target sequence, wherein the upstream and downstream ends of the target sequence comprise a contiguous sequence of the supercoiled DNA and wherein the annealed single stranded RNA oligonucleotide produces a forced open promoter complex.

26. The method of claim 25, wherein the single stranded RNA oligonucleotide comprises an intervening connecter sequence that connects the 5' end to the 3' end that lacks complementarity with the supercoiled DNA.

27. The method of claim 25, wherein the RNA oligonucleotide comprises at least 20 nucleotides.

28. The method of claim 25, wherein the RNA oligonucleotide comprises at least 30 nucleotides.

29. The method of claim 26, wherein the intervening connecting sequence comprises a sequence that is useful for targeting or transcriptional purposes.

30. The method of claim 29, wherein the intervening connecting sequence comprises a sequence that promotes binding of a polymerase or a transcription factor.

31. The method of claim 30, wherein said polymerase is an RNA polymerase.

32. The method of claim 25, wherein the target sequence is a TATA or CAT box that is upstream from the transcription initiation site of the nucleic acid sequence.

33. The method of claim 25, wherein annealing the RNA oligonucleotide to the supercoiled DNA promotes an increase in the expression of the nucleic acid sequence relative to the expression of nucleic acid sequence in a supercoiled DNA lacking an annealed RNA oligonucleotide.

34. The method of claim 25, wherein the RNA oligonucleotide does not anneal downstream of the −1 position.

35. The method of claim 25, wherein the RNA oligonucleotide is annealed to the non-coding strand of the supercoiled DNA.

36. The method of claim 25, wherein the RNA oligonucleotide is annealed to the coding strand of the supercoiled DNA.

* * * * *

SEQUENCE LISTING

```
<160> NUMBER OF SEQ ID NOS: 14

<210> SEQ ID NO 1
<211> LENGTH: 1170
<212> TYPE: DNA
<213> ORGANISM: Homo sapiens

<400> SEQUENCE: 1
cgtgaggctc cggtgcccgt cagtgggcag agcgcacatc gcccacagtc cccgagaagt      60
tggggggagg ggtcggcaat tgaaccggtg cctagagaag gtgcgcggg gtaaactggg      120 aaagtgatgt cgtgtactgg ctccgccttt ttcccgaggg tggggagaa ccgtatataa      180 gtgcagtagt cgccgtgaac gttcttttttc gcaacgggtt tgccgccaga acacaggtaa    240
gtgccgtgtg tggttcccgc gggcctggcc tctttacggg ttatggccct tgcgtgcctt    300
gaattacttc cacctggctc cagtacgtga ttcttgatcc cgagctggag ccaggggcgg    360
gccttgcgct ttaggagccc cttcgcctcg tgcttgagtt gaggcctggc ctgggcgctg    420
gggccgccgc gtgcgaatct ggtggcacct tcgcgcctgt ctcgctgctt tcgataagtc    480
tctagccatt taaaattttt gatgacctgc tgcgacgctt tttttctggc aagatagtct   540
tgtaaatgcg ggccaggatc tgcacactgg tatttcggtt tttgggcccg cggccggcga   600
cggggcccgt gcgtcccagc gcacatgttc ggcgaggcgg ggcctgcgag cgcggccacc   660
gagaatcgga cgggggtagt ctcaagctgg ccggcctgct ctggtgcctg gcctcgcgcc   720
gccgtgtatc gccccgccct gggcggcaag gctggcccgg tcggcaccag ttgcgtgagc   780
ggaaagatgg ccgcttcccg gccctgctcc aggggctca aaatggagga cgcggcgctc   840
gggagagcgg gcgggtgagt cacccacaca aaggaaaagg gcctttccgt cctcagccgt   900
cgcttcatgt gactccacgg agtaccgggc gccgtccagg cacctcgatt agttctggag   960
```

```
ctttggagt acgtcgtctt taggttgggg ggaggggttt tatgcgatgg agtttcccca    1020
cactgagtgg gtggagactg aagttaggcc agcttggcac ttgatgtaat tctccttgga    1080
atttggcctt tttgagtttg gatcttggtt cattctcaag cctcagacag tggttcaaag    1140 ttttttctt ccatttcagg tgtcgtgaac                                      1170

<210> SEQ ID NO 2
<211> LENGTH: 203
<212> TYPE: DNA
<213> ORGANISM: Homo sapiens

<400> SEQUENCE: 2
gtgaggctcc ggtgcccgtc agtgggcaga gcgcacatcg cccacagtcc ccgagaagtt    60
gggggagggg tcggcaatt gaaccggtgc ctagagaagg tggcgcgggg taaactggga    120
aagtgatgtc gtgtactggc tccgcctttt tcccgagggt gggggagaac cgtatataag    180
tgcagtagtc gccgtgaacg ttc                                            203

<210> SEQ ID NO 3
<211> LENGTH: 20
<212> TYPE: DNA
<213> ORGANISM: Homo sapiens

<400> SEQUENCE: 3
tggcacatgg ccaatgcatt                                                20

<210> SEQ ID NO 4
<211> LENGTH: 21
<212> TYPE: DNA
<213> ORGANISM: Homo sapiens

<400> SEQUENCE: 4
ggcggagttg ttacgacatt t                                              21

<210> SEQ ID NO 5
<211> LENGTH: 21
<212> TYPE: DNA
<213> ORGANISM: Homo sapiens

<400> SEQUENCE: 5
cggttcacta aacgagctct g                                              21

<210> SEQ ID NO 6
<211> LENGTH: 46
<212> TYPE: DNA
<213> ORGANISM: Homo sapiens

<400> SEQUENCE: 6
tgcttatata gacctcccac cgtacacgcc taccgcccat ttgcgt                   46

<210> SEQ ID NO 7
<211> LENGTH: 46
<212> TYPE: DNA
<213> ORGANISM: Homo sapiens

<400> SEQUENCE: 7
cggttcacta aacgagctct gcttatatag acctcccacc gtacac                   46

<210> SEQ ID NO 8
<211> LENGTH: 46
<212> TYPE: DNA
```

```
<213> ORGANISM: Homo sapiens

<400> SEQUENCE: 8
gatggcgtct ccaggcgatc tgacggttca ctaaacgagc tctgct              46

<210> SEQ ID NO 9
<211> LENGTH: 54
<212> TYPE: DNA
<213> ORGANISM: Homo sapiens

<400> SEQUENCE: 9
gatgatcgga tcgagtcgga gatcgatgga tcggatcgga tcgagtcgag tcag     54

<210> SEQ ID NO 10
<211> LENGTH: 112
<212> TYPE: DNA
<213> ORGANISM: Homo sapiens

<400> SEQUENCE: 10
gtgtacggtg ggaggtctat ataagcagtc gagttaatta acggccgtct agaggtaccg    60
aattcgctag cgcggccgcc gatcggtcga cggacgcaaa tgggcggtag gc           112

<210> SEQ ID NO 11
<211> LENGTH: 20
<212> TYPE: DNA
<213> ORGANISM: Unknown
<220> FEATURE:
<223> OTHER INFORMATION: Hypothetical padlock DNA sequence

<400> SEQUENCE: 11
catgcctcag gtcgactcga                                          20

<210> SEQ ID NO 12
<211> LENGTH: 21
<212> TYPE: DNA
<213> ORGANISM: Unknown
<220> FEATURE:
<223> OTHER INFORMATION: Hypothetical padlock DNA sequence

<400> SEQUENCE: 12
acgaggccag tgccaagctt g                                        21

<210> SEQ ID NO 13
<211> LENGTH: 50
<212> TYPE: DNA
<213> ORGANISM: Unknown
<220> FEATURE:
<223> OTHER INFORMATION: Hypothetical padlock target DNA sequence

<400> SEQUENCE: 13
gatcgcgagt cgacctgagg catgcaagct tggcactggc ctcgtgtttt         50

<210> SEQ ID NO 14
<211> LENGTH: 41
<212> TYPE: DNA
<213> ORGANISM: Unknown
<220> FEATURE:
<223> OTHER INFORMATION: Hypothetical padlock DNA sequence

<400> SEQUENCE: 14
acgaggccag tgccaagctt gcatgcctca ggtcgactcg a                  41
```